United States Patent
Hovland et al.

(10) Patent No.: US 8,500,626 B2
(45) Date of Patent: Aug. 6, 2013

(54) SYSTEM AND METHOD FOR TREATING AND/OR PREVENTING ERECTION PROBLEMS

(75) Inventors: Claire Thomas Hovland, Andover, MN (US); Curtis Eugene Olson, St. Paul, MN (US); Irwin Goldstein, San Diego, CA (US); Noel N. Kim, San Diego, CA (US)

(73) Assignee: Alagin Research LLC, San Diego, CA (US)

( * ) Notice: Subject to any disclaimer, the term of this patent is extended or adjusted under 35 U.S.C. 154(b) by 905 days.

(21) Appl. No.: 12/453,526

(22) Filed: May 14, 2009

(65) Prior Publication Data
US 2010/0041943 A1 Feb. 18, 2010

Related U.S. Application Data

(60) Provisional application No. 61/053,272, filed on May 15, 2008, provisional application No. 61/076,958, filed on Jun. 30, 2008, provisional application No. 61/202,513, filed on Mar. 6, 2009.

(51) Int. Cl.
*A61F 5/00* (2006.01)
(52) U.S. Cl.
USPC .......................................................... 600/38
(58) Field of Classification Search
USPC ................................ 600/38–40; 128/897, 898
See application file for complete search history.

(56) References Cited

U.S. PATENT DOCUMENTS

| | | | |
|---|---|---|---|
| 4,509,512 A | 4/1985 | LeClercq | |
| 4,836,192 A | 6/1989 | Abbate | |
| 4,988,336 A | 1/1991 | Kohn | |
| 5,421,808 A * | 6/1995 | Osbon et al. | 600/38 |
| 5,531,226 A | 7/1996 | Harris | |
| 5,536,233 A * | 7/1996 | Khouri | 600/38 |
| 5,571,084 A | 11/1996 | Palmer | |
| 5,669,869 A * | 9/1997 | Strom | 600/38 |
| 5,695,446 A * | 12/1997 | Lindholm-Ventola | 600/38 |
| 6,030,318 A | 2/2000 | Howard | |
| 6,183,414 B1 * | 2/2001 | Wysor et al. | 600/38 |
| 6,547,756 B1 | 4/2003 | Greter et al. | |
| 6,551,280 B1 | 4/2003 | Knighton et al. | |
| 6,676,631 B1 | 1/2004 | Greter | |
| 6,905,459 B2 * | 6/2005 | Humphries, Jr. | 600/38 |
| 7,037,256 B2 | 5/2006 | Osbon et al. | |
| 7,572,220 B2 * | 8/2009 | Nan | 600/38 |
| 8,187,165 B2 * | 5/2012 | Park | 600/41 |
| 2005/0119521 A1 * | 6/2005 | Pitcher | 600/38 |

OTHER PUBLICATIONS

RigiScan® Plus User Guide © 1995 Dacomed Corporation.
Pilot Study of Changes in Stretched Penile Length 3 Months after Radical Retropubic Prostatectomy, by M. D. Munding et al. (2001) Urology, vol. 58, p. 567-569.

(Continued)

*Primary Examiner* — Samuel Gilbert
(74) *Attorney, Agent, or Firm* — Greenblum & Bernstein, P.L.C.

(57) ABSTRACT

A system for causing penile erection and/or subjecting the penis to stretching. The system utilizes a vacuum source and/or supply device, a housing configured to at least partially receive therein a penis, and a garment or support configured to retain and/or support the housing. Also disclosed is a method of using the system on a user's penis as discussed in the instant application.

26 Claims, 36 Drawing Sheets

OTHER PUBLICATIONS

Early Use of Vacuum Constriction Device Following Radical Prostatectomy Facilitates Early Sexual Activity and Potentially Earlier Return of Erectile Function, by R. Raina et al., International Journal of Impotence Research (2006), vol. 18, p. 77-81.

Effect of Penile Size on Nocturnal Erections: Evaluation with NPTR Testing with Men Having Micropenis, by O. Yaman et al., International Journal of Impotence Research (2005), vol. 17, p. 243-247.

New Insights into the Pathogenesis of Penile Shortening After Radical Prostatectomy and the Role of Postoperative Sexual Function, by P. Gontero et al., The Journal of Urology (2007), vol. 178, p. 602-607.

Nocturnal Tumescence: A Parameter for Postoperative Erectile Integrity after Nerve Sparing Radical Prostatectomy, by a. Bannowsky et al., The Journal of Urology (2006), vol. 175, p. 2214-2217.

A Prospective Study Measuring Penile Length in Men Treated With Radical Prostatectomy for Prostate Cancer, by M. Savoie et al., The Journal of Urology (2003), vol. 169, p. 1462-1464.

Lengthening Shortening Penis Caused by Peyronie's Disease Using Circular Venous Grafting and Daily Stretching With a Vacuum Erection Device, by T. F. Lue et al., The Journal of Urology (1999), vol. 161, p. 1141- 1144.

Preserved Postoperative Penile Size Correlates Well with Maintained Erectile Function after Bilateral Nerve-Sparing Radical Retropubic Prostatectomy, by A. Briganti et al., European Urology (2007), vol. 52, p. 702-707.

Preservation of Penile Length after Radical Prostatectomy: Early Intervention with a Vacuum Erection Device, by BL Dalkin et al., International Journal of Impotence Research (2007), 19, p. 501-504.

Sildenafil Citrate and Vacuum Constriction Device Combination Enhances Sexual Satisfaction in Erectile Dysfunction after Radical Prostatectomy, by R. Raina et al. (2005) Urology, vol. 65, p. 360-364.

Unusual Complications of the Vacuum Erection Device, by J. P. Ganem et al. (1998) Urology, vol. 51, p. 627-631.

A Vacuum Device for Penile Elongation: Fact or Fiction?, by M. K. Aghamir et al. (2006) BJU International, vol. 97, p. 777-778.

Hemodynamics of Penile Erection: III. Measurement of Deep Intracavernosal and Subtunical Blood Flow and Oxygen Tension, by K. M. Azadzoi et al., The Journal of Urology (1995), vol. 153, p. 521-526.

Vasculogenic Impotence and Cavernosal Oxygen Tension, by SL Brown et al., International Journal of Impotence Research (2000), vol. 12, p. 19-22.

Prostanoid Production in Rabbit Corpus Cavernosum: I. Regulation by Oxygen Tension, by J. T. Daley et al., The Journal of Urology (1996), vol. 155, p. 1482-1487.

Alterations in Angiogenic Growth Factors and Neuronal Nitric Oxide Synthase Expression in Chronic Cavernosal Ischemia, by T. Wang et al., International Journal of Impotence Research (2004), 16, p. 403-411.

Oxygen Tension Regulates the Nitric Oxide Pathway, by N. Kim et al., The Journal of Clinical Investigation (1993), vol. 91, p. 437-442.

$O_2$-Dependent Prostanoid Synthesis Activates Functional PGE Receptors on Corpus Cavernosum Smooth Muscle, by R. B. Moreland et al., American Journal of Physiology—Heart Circulatory Physiology (2001), vol. 281, H552-H558.

Is There a Role of Hypoxemia in Penile Fibrosis; a Viewpoint Presented to the Society for the Study of Impotence, by RB Moreland, International Journal of Impotence Research (1998), vol. 10, p. 113-120.

Pathophysiology of Erectile Dysfunction: the Contributions of Trabecular Structure to Function and the Role of Functional Antagonism, by RB Moreland, International Journal of Impotence Research (2000), vol. 12, Suppl 4, S39-S46.

Penile Rehabilitation Should Become the Norm for Radical Prostatectomy Patients, by J. P. Mulhall et al., The Journal of Sexual Medicine (2007), vol. 4, p. 538-543.

The Effect of Hyperbaric Oxygen Therapy on Erectile Function Recovery in a Rat Cavernous Nerve Injury Model, by A. Muller et al., The Journal of Sexual Medicine (2008), vol. 5, p. 562-570.

Penile Oxygen Saturation in the Flaccid and Erect Penis in Men with and without Erectile Dysfunction, by P. Padmanabhan et al., Journal of Andrology (2007), vol. 28, No. 2, p. 223-228.

Blood Gas Changes in the Corpora Cavernosa: Metabolic and Histomorphometric Implications in the Patient with Erectile Dysfunction, by F. Sasso et al., The Journal of Urology (2003), vol. 169, p. 2270-2274.

Cavernous Oxygen Tension and Smooth Muscle Fibers: Relation and Function, by A. A. Sattar et al., The Journal of Urology (1995), vol. 154, p. 1736-1739.

Cavernous Oxygen Tension in the Patients with Erectile Dysfunction, by F. Tarhan et al., International Journal of Impotence Research (1997), 9, p. 149-153.

Six sheets of drawings showing a prior art vacuum erection device dated Jan. 2007.

* cited by examiner

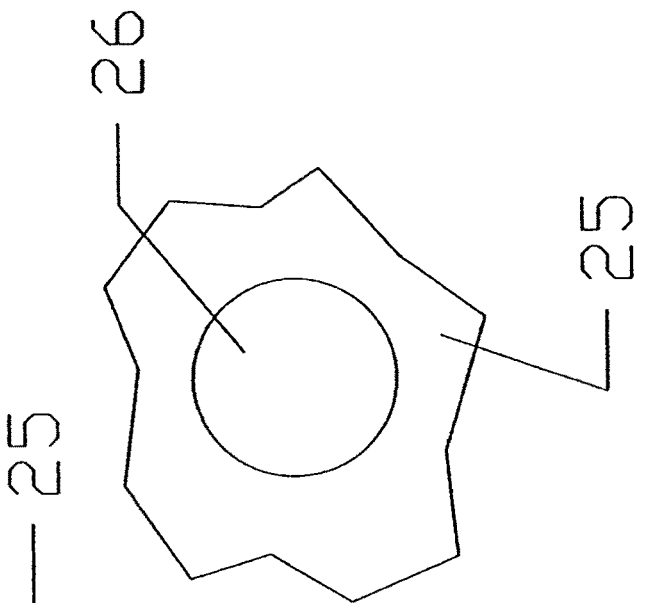
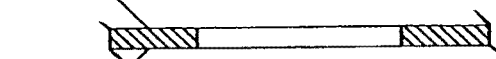
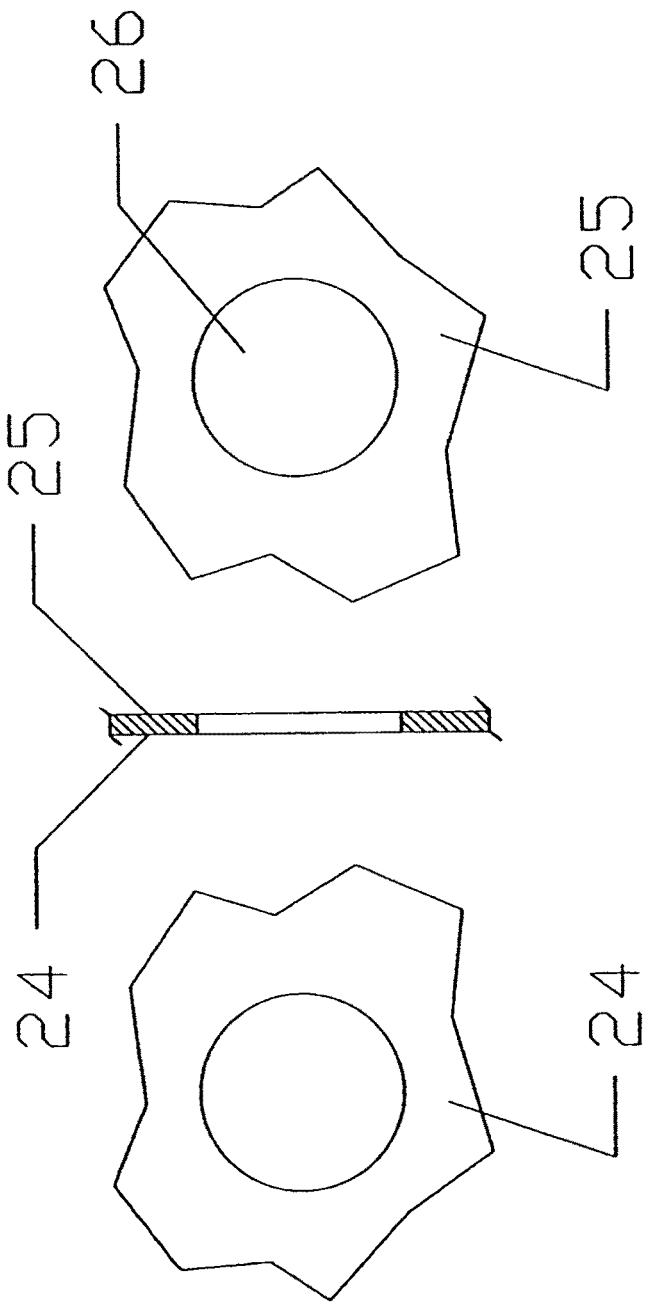

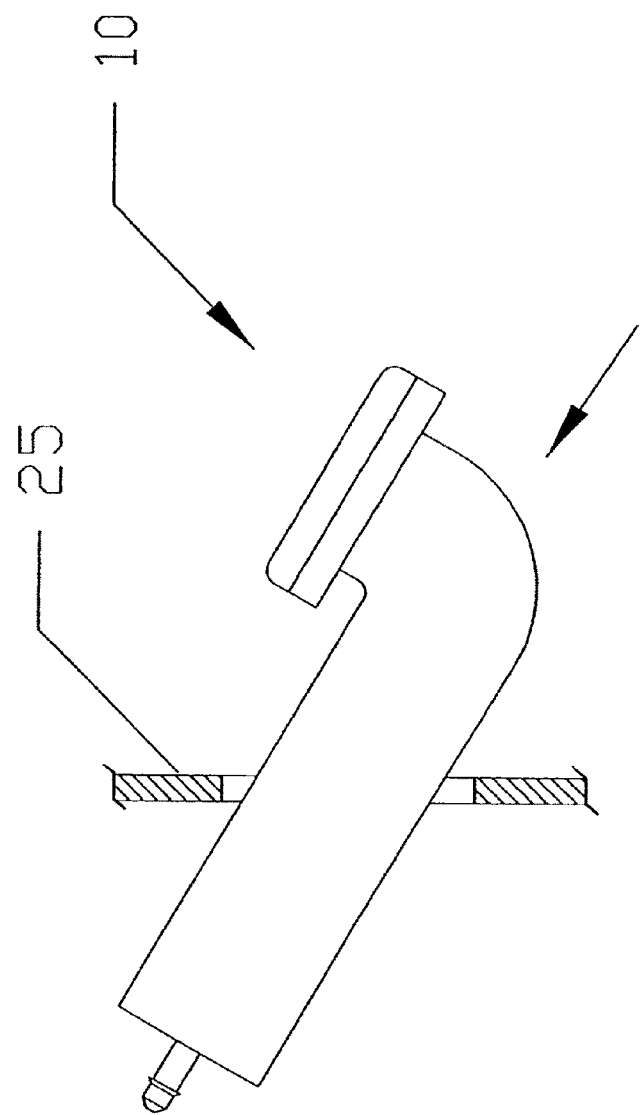

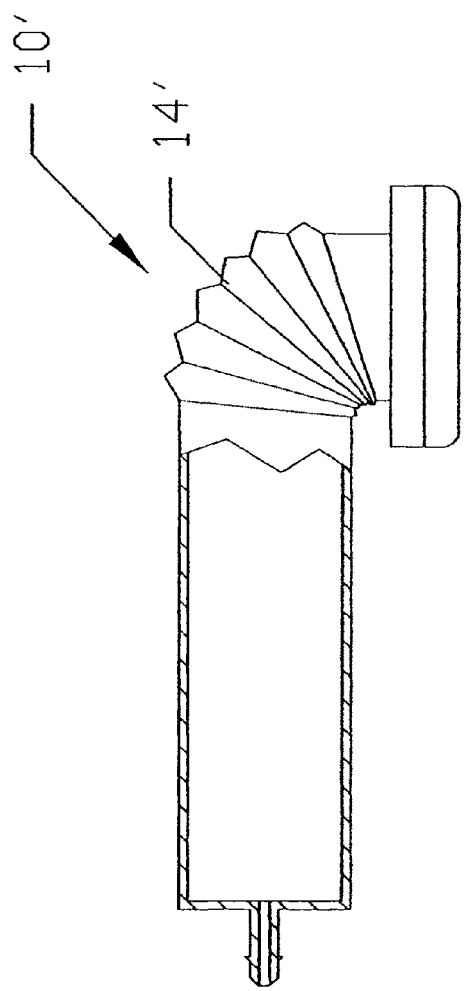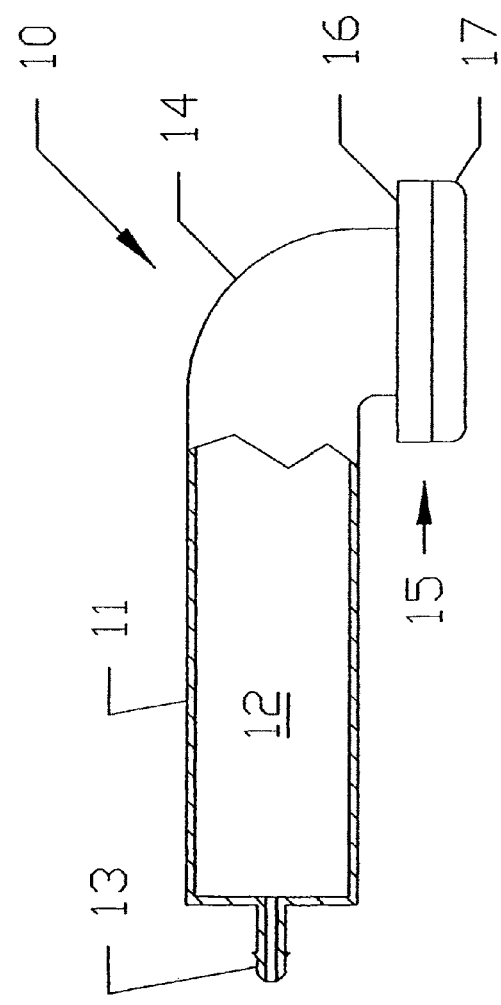

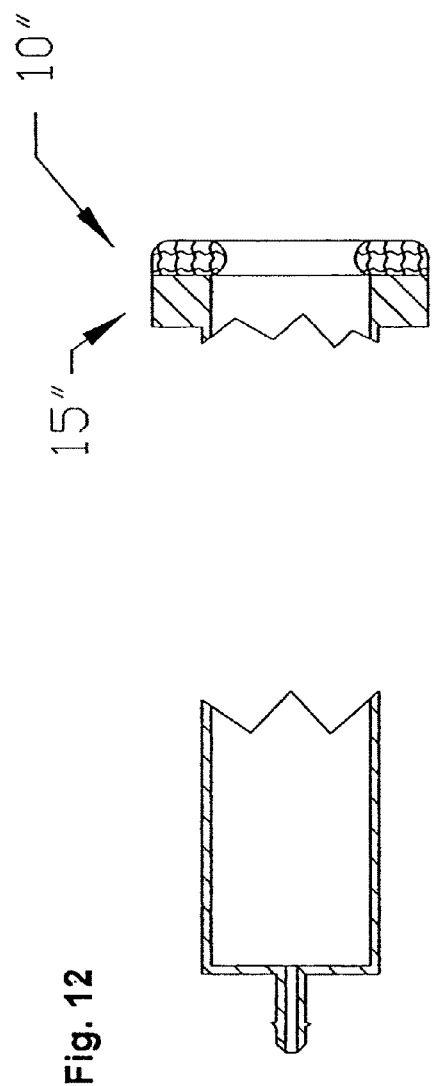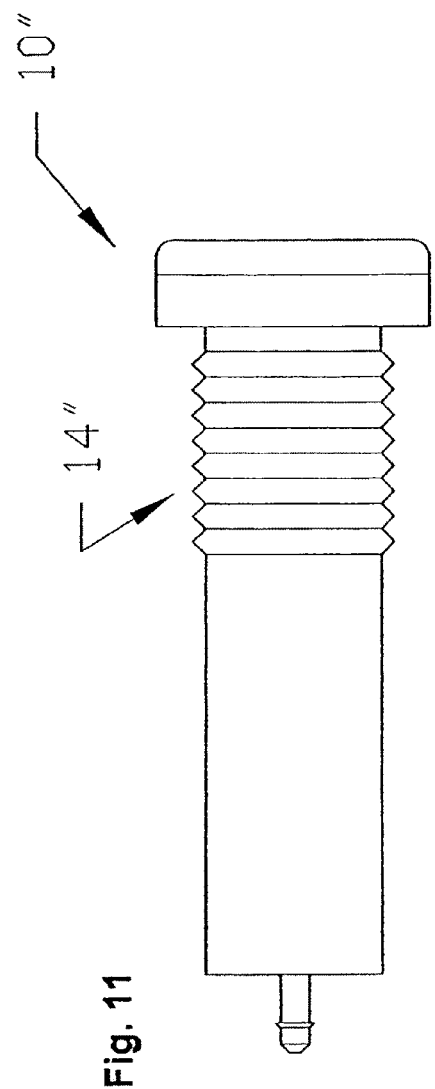

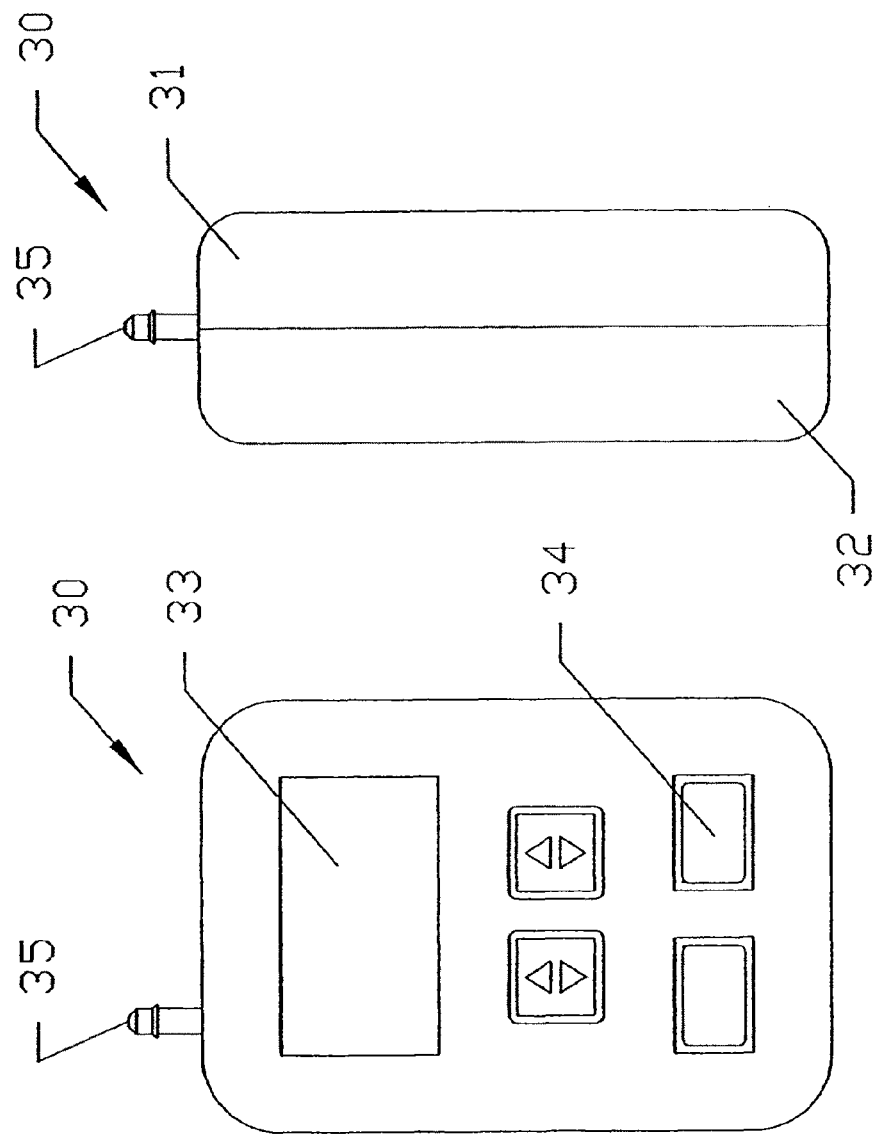

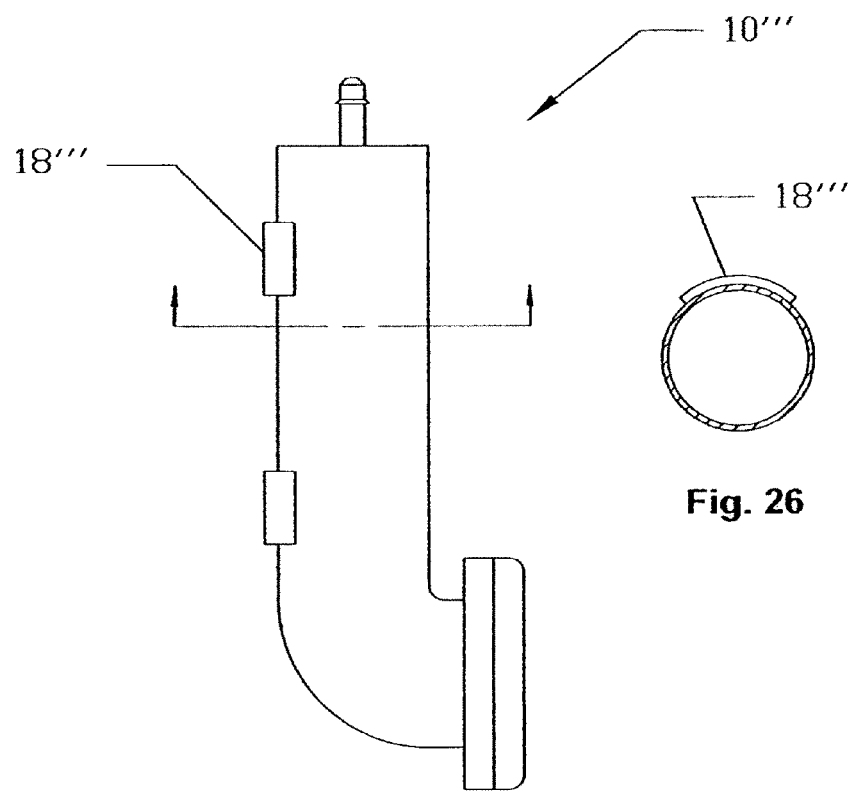

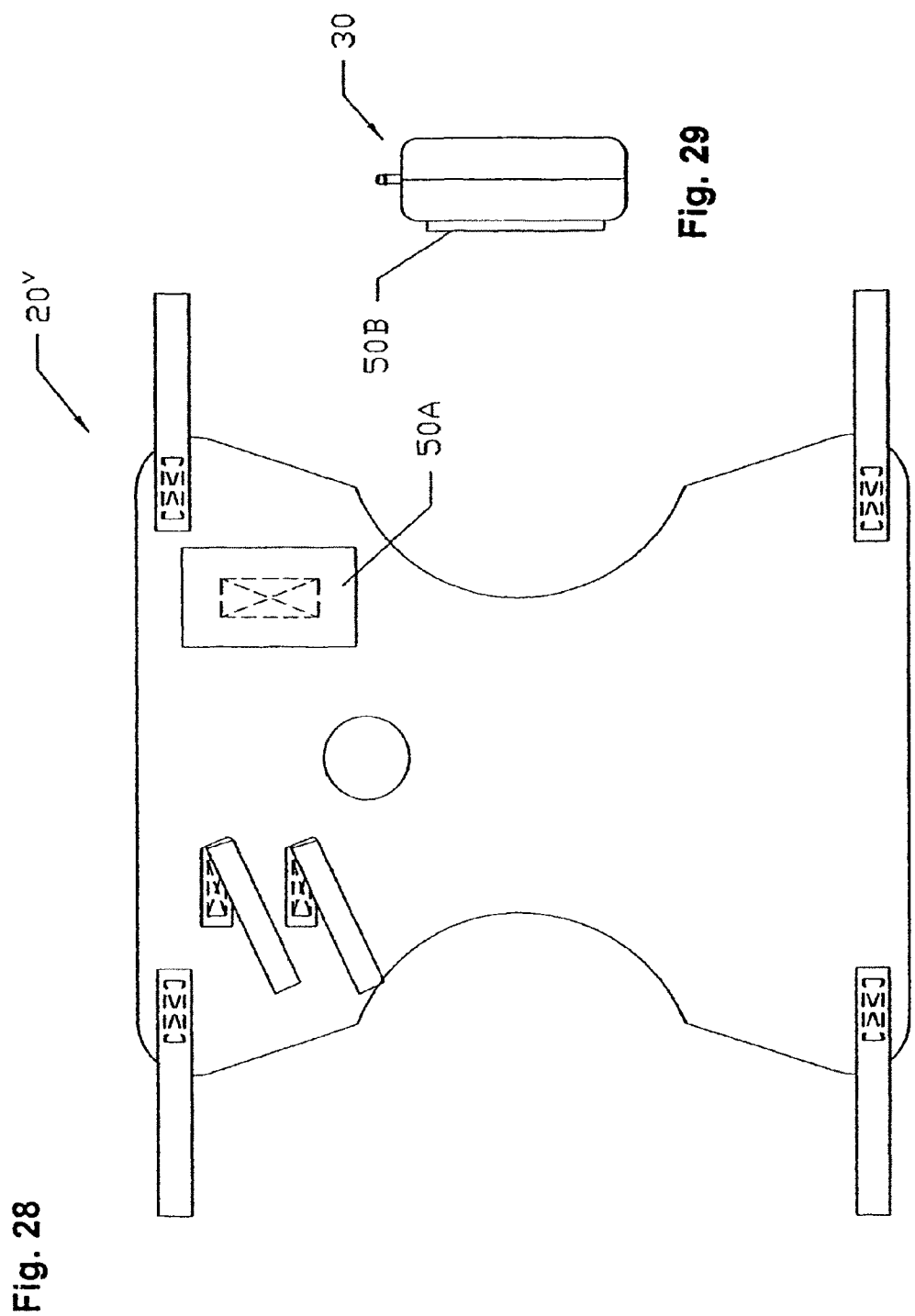

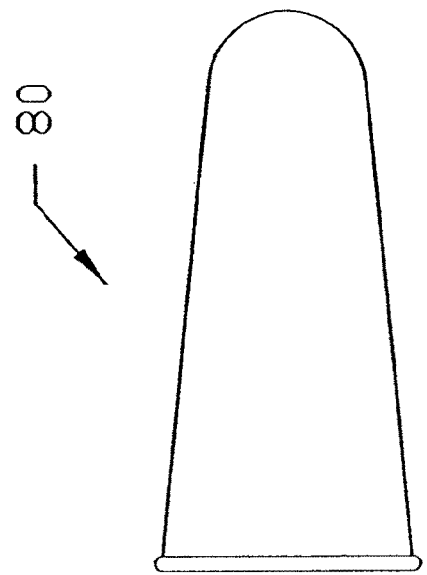
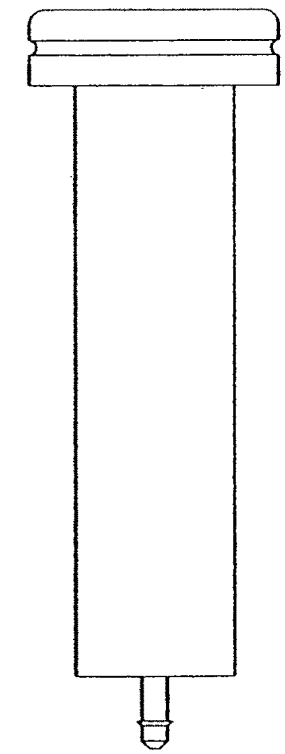
Fig. 38
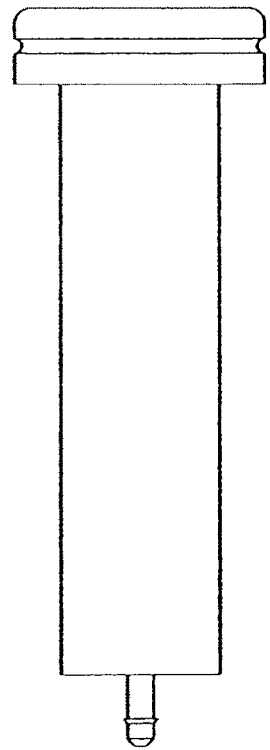
Fig. 39

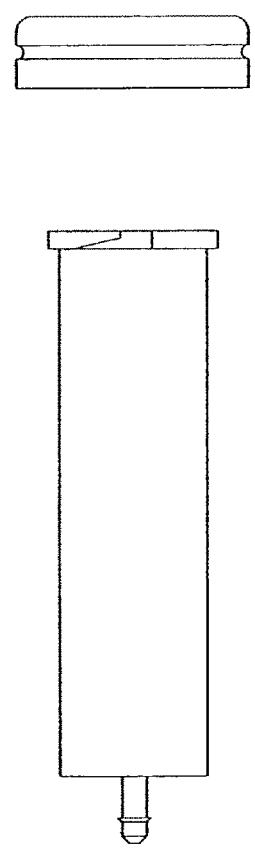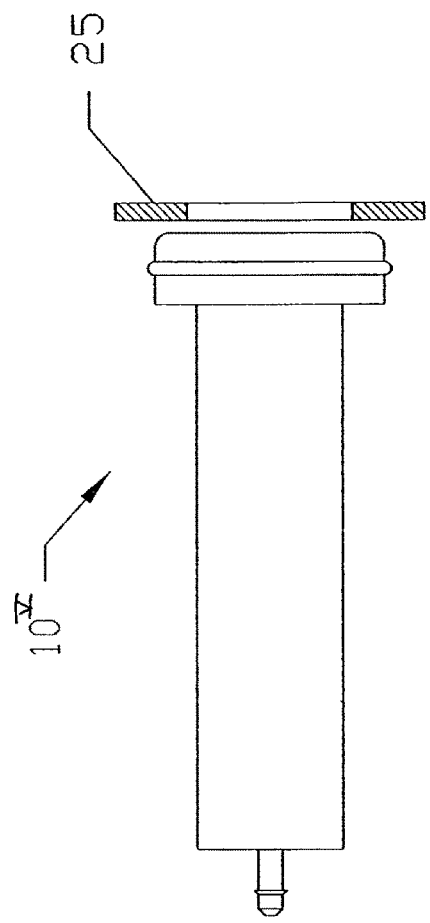
Fig. 41
Fig. 42

SYSTEM AND METHOD FOR TREATING AND/OR PREVENTING ERECTION PROBLEMS

CROSS-REFERENCE TO RELATED APPLICATIONS

The present application claims the benefit of U.S. Provisional Patent Application Nos. 61/053,272 filed on May 15, 2008, 61/076,958 filed on Jun. 30, 2008, and 61/202,513 filed on Mar. 6, 2009 under 35 U.S.C. §119(e), the disclosures of which are each expressly incorporated by reference herein in their entireties.

BACKGROUND OF THE INVENTION

1. Field of the Invention

The invention relates to a system for causing penile erection wherein the system includes a vacuum source and/or supply device, a housing configured to at least partially receive therein a penis, and a garment or support configured to retain and/or support the housing. The invention also relates to a system for causing penile erections, wherein the system includes a housing configured to at least partially receive therein a penis and a garment or wearable support configured to retain and/or support the housing. The invention further also relates to a method of causing penile erections, wherein the method includes positioning a garment or support on a user, whereby the garment or support is configured to retain and/or support a housing which at least partially receives therein the user's penis. The invention additionally relates to a method of causing penile erections, wherein the method includes placing a housing at least partially over or covering a user's penis, supporting the housing on the user in a hands-free manner, and producing a vacuum in the housing for at least one predetermined time period while the user is at least one of sleeping, oriented in a generally horizontal position, and being treated for a condition which results in the user having lost, at least partially, an ability to achieve an erection at least during sleep, and specifically (rapid eye movement) REM sleep. The invention also relates to a method of treating a medical condition, wherein the method includes causing a vacuum in a housing for at least one predetermined time period while the housing is at least partially arranged over or on the user's penis in a hands-free manner. The medical condition may be a condition which results in a user having lost, at least partially, an ability to achieve an erection at least during sleep, and specifically REM sleep. The invention also relates to a method of treating the dysfunction, diminished, or loss of nocturnal penile tumescence (NPT) and/or erectile dysfunction (ED), which can result from, among other things, a surgical procedure such as, e.g., radical retropubic prostatectomy. The invention also relates to a method and/or device which can treat the potential loss of penile length that can result from the patient having diminished NPT and/or ED. The invention also provides for a system and method for treating disease states that result in ED and/or penile shortening. The invention also provides for a system and method for rehabilitating the penis. The invention also provides for a system and method for preventing ED and/or penile shortening. The invention also provides for a system and method for stretching the penis to prevent and/or treat, among other things, ED and/or penile shortening. The invention also provides for a system and method for simulating natural erections in order to prevent and/or treat, among other things, ED and/or penile shortening.

2. Discussion of Background Information

Nocturnal penile tumescence (NPT) is a natural or normal spontaneous occurrence of an erection of the penis during sleep. Such NPT events result in regular and intermittent erectile activity which is important for maintaining erectile tissue viability and sexual function in men. An NPT event is characterized by the man achieving an erection and maintaining it for between about twenty minutes and about forty minutes. For example, during a typical eight hour sleep, men (on average) can have four erectile episodes each lasting up to about 45 minutes. This results in a total duration of about three hours of penile erection. NPT events are also characterized by normal and healthy blood flow to the penis with the penile blood having good or normal oxygenation. Men typically experience several NPT episodes during night-time sleep, and more specifically, during rapid eye movement (REM) sleep. Men with erectile dysfunction (ED) can have diminished to non-existent NPT. It is even believed that NPT events play a role in restoring and/or maintaining penile length. Thus, if a man experiences diminished or loss of NPT, especially as a result of or in combination with ED, he may experience a loss of some, or even significant amount, of penile length. The health of the penis may also suffer from not having normal and healthy blood flow to the penis which typically occurs with NPT. The loss of penile length can, in particular, be a significant negative side-effect of having diminished NPT and ED. As such, it would be desirable to provide a treatment which can, among other things, restore and/or provide normal and healthy blood flow (and/or oxygenation and/or stretching) to the penis and/or which can restore or maintain penile length.

Devices are known which can detect whether a man has diminished to non-existent NPT. Typically, a device is placed around the penis during sleep to detect changes in girth. Information from the device is provided to a computer for analysis. If no nocturnal tumescence is detected, if the man has been diagnosed with ED, and/or if the man would like to address loss of penile length possibly resulting therefrom, the man may be a candidate for using the invention.

Furthermore, it is known that "stretching" is a natural consequence of penile erection or tumescence. In fact, known devices function mainly to stretch the penis by subjecting it to vacuum.

The invention acknowledges the following documents which are each hereby expressly incorporated by reference herein in their entireties:
RigiScan® Plus User Guide © 1995 Dacomed Corporation;
U.S. Pat. No. 4,509,512 to LeClercq issued on Apr. 9, 1985;
U.S. Pat. No. 5,531,226 to Harris issued on Jul. 2, 1996;
U.S. Pat. No. 6,030,318 to Howard issued on Feb. 29, 2000;
U.S. Pat. No. 4,988,336 to Kohn issued on Jan. 29, 1991;
U.S. Pat. No. 7,037,256 to Osbon et al. issued on May 2, 2006;
U.S. Pat. No. 6,183,414 to Wysor et al. issued on Feb. 6, 2001;
U.S. Pat. No. 6,551,280 to Knighton et al. issued on Apr. 22, 2003;
Pilot Study of Changes in Stretched Penile Length 3 Months after Radical Retropubic Prostatectomy, by M. D. Munding et al. (2001) Urology, Vol. 58, p 567-569;
Early Use of Vacuum Constriction Device Following Radical Prostatectomy Facilitates Early Sexual Activity and Potentially Earlier Return of Erectile Function, by R. Raina et al., International Journal of Impotence Research (2006), Vol. 18, p 77-81;

Effect of Penile Size on Nocturnal Erections: Evaluation with NPTR Testing with Men Having Micropenis, by O. Yaman et al., International Journal of Impotence Research (2005), Vol. 17, p 243-247;

New Insights into the Pathogenesis of Penile Shortening After Radical Prostatectomy and the Role of Postoperative Sexual Function, by P. Gontero et al., The Journal of Urology (2007), Vol. 178, p 602-607;

Nocturnal Tumescence: A Parameter for Postoperative Erectile Integrity after Nerve Sparing Radical Prostatectomy, by A. Bannowsky et al., The Journal of Urology (2006), Vol. 175, p 2214-2217;

A Prospective Study Measuring Penile Length in Men Treated With Radical Prostatectomy for Prostate Cancer, by M. Savoie et al., The Journal of Urology (2003), Vol. 169, p 1462-1464;

Lengthening Shortening Penis Caused by Peyronie's Disease Using Circular Venous Grafting and Daily Stretching With A Vacuum Erection Device, by T. F. Lue et al., The Journal of Urology (1999), Vol. 161, p 1141-1144;

Preserved Postoperative Penile Size Correlates Well with Maintained Erectile Function after Bilateral Nerve-Sparing Radical Retropubic Prostatectomy, by A. Briganti et al., European Urology (2007), Vol. 52, p 702-707;

Preservation of Penile Length after Radical Prostatectomy: Early Intervention with a Vacuum Erection Device, by B L Dalkin et al., International Journal of Impotence Research (2007), 19, p 501-504;

Sildenafil Citrate and Vacuum Constriction Device Combination Enhances Sexual Satisfaction in Erectile Dysfunction after Radical Prostatectomy, by R. Raina et al. (2005) Urology, Vol. 65, p 360-364;

Unusual Complications of the Vacuum Erection Device, by J. P. Ganem et al. (1998) Urology, Vol. 51, p 627-631;

A Vacuum Device for Penile Elongation: Fact or Fiction?, by M. K. Aghamir et al. (2006) BJU International, Vol. 97, p 777-778;

Hemodynamics of Penile Erection: III. Measurement of Deep Intracavernosal and Subtunical Blood Flow and Oxygen Tension, by K. M. Azadzoi et al., The Journal of Urology (1995), Vol. 153, p 521-526;

Vasculogenic Impotence and Cavernosal Oxygen Tension, by S L Brown et al., International Journal of Impotence Research (2000), Vol. 12, p 19-22;

Prostanoid Production in Rabbit Corpus Cavernosum: I. Regulation By Oxygen Tension, by J. T. Daley et al., The Journal of Urology (1996), Vol. 155, p 1482-1487;

Alterations in Angiogenic Growth Factors and Neuronal Nitric Oxide Synthase Expression in Chronic Cavernosal Ischemia, by T. Wang et al., International Journal of Impotence Research (2004), 16, p 403-411;

Oxygen Tension Regulates the Nitric Oxide Pathway, by N. Kim et al., The Journal of Clinical Investigation (1993), Vol. 91, p 437-442;

$O_2$-Dependent Prostanoid Synthesis Activates Functional PGE Receptors on Corpus Cavernosum Smooth Muscle, by R. B. Moreland et al., American Journal of Physiology—Heart Circulatory Physiology (2001), Vol. 281, H552-H558;

Is There a Role of Hypoxemia in Penile Fibrosis; a Viewpoint Presented to the Society for the Study of Impotence, by R B Moreland, International Journal of Impotence Research (1998), Vol. 10, p 113-120;

Pathophysiology of Erectile Dysfunction: the Contributions of Trabecular Structure to Function and the Role of Functional Antagonism, by R B Moreland, International Journal of Impotence Research (2000), Vol. 12, Suppl 4, S39-S46;

Penile Rehabilitation Should Become the Norm for Radical Prostatectomy Patients, by J. P. Mulhall et al., The Journal of Sexual Medicine (2007), Vol. 4, p 538-543;

The Effect of Hyperbaric Oxygen Therapy on Erectile Function Recovery in a Rat Cavernous Nerve Injury Model, by A. Muller et al., The Journal of Sexual Medicine (2008), Vol. 5, p 562-570;

Penile Oxygen Saturation in the Flaccid and Erect Penis in Men with and without Erectile Dysfunction, by P. Padmanabhan et al., Journal of Andrology (2007), Vol. 28, No. 2, p 223-228;

Blood Gas Changes in the Corpora Cavernosa: Metabolic and Histomorphometric Implications in the Patient with Erectile Dysfunction, by F. Sasso et al., The Journal of Urology (2003), Vol. 169, p 2270-2274;

Cavernous Oxygen Tension and Smooth Muscle Fibers: Relation and Function, by A. A. Sattar et al., The Journal of Urology (1995), Vol. 154, p 1736-1739; and Cavernous Oxygen Tension in the Patients with Erectile Dysfunction, by F. Tarhan et al., International Journal of Impotence Research (1997), 9, p 149-153.

SUMMARY OF THE INVENTION

The invention relates to a system for causing penile erection wherein the system includes a vacuum source and/or supply device, a housing configured to at least partially receive therein a penis, and a garment or support configured to retain and/or support the housing.

The invention also relates to a system for causing penile erection which addresses, treats, or attempts to treat, one or more symptoms and/or problems identified in the above-noted non-patent literature, which are each hereby expressly incorporated by reference herein in their entireties.

The invention also relates to a system for causing penile erection which addresses, treats, or attempts to treat, one or more conditions (which effect or are affected by erections) that may be caused by aging, disease or medical/surgical interventions.

The invention also relates to a method of treating the dysfunction, diminished, or loss of nocturnal penile tumescence (NPT), erectile dysfunction (ED), and/or preventing penile shortening (maintaining penile length) which can result from, among other things, a surgical procedure such as, e.g., radical retropubic prostatectomy.

The invention also relates to a method and/or device which can treat males having diminished NPT and/or ED following surgery or as treatment for a disease that diminishes penile blood flow or nerve function.

The invention also provides for a system and method for treating disease states that result in ED and/or penile shortening. The invention also provides for a system and method for rehabilitating the penis. The invention also provides for a system and method for preventing ED and/or penile shortening. The invention also provides for a system and method for stretching the penis to prevent and/or treat, among other things, ED and/or penile shortening. The invention also provides for a system and method for simulating natural erections in order to prevent and/or treat, among other things, ED and/or penile shortening. The invention also provides for a system and method for subjecting the penis to stretching that simulates natural consequence of penile erection or tumescence.

The invention also provides for a system and method for subjecting the penis to "repetitive" events that cause or simulate tumescence and/or increased blood flow and/or oxygenation and/or stretching wherein the device of the system or method utilizes repeated vacuum cycles in a hands-free manner.

The invention relates to a system for causing penile erection, wherein the system includes a housing configured to at least partially receive therein a penis and a garment or wearable support configured to retain and/or support the housing.

The invention relates to a method of causing penile erection, wherein the method includes positioning a garment or support on a user, whereby the garment or support is configured to retain and/or support a housing which at least partially receives therein the user's penis.

The invention relates to a method of causing penile erection, wherein the method includes placing a housing at least partially over or covering a user's penis, supporting the housing on the user in a hands-free manner, and causing a vacuum in the housing for at least one predetermined time period while the user is at least one of; sleeping, positioned in a generally horizontal position, and being treated for a condition which results in the user having lost, at least partially, the ability to achieve an erection at least during sleep.

The invention relates to a method of treatment for a medical condition, wherein the method includes causing a vacuum in a housing for at least one predetermined time period while the housing is at least partially arranged over or on the user's penis in a hands-free manner.

The medical condition may be a condition which results in a user having lost, at least partially, the ability to achieve an erection at least during sleep.

The invention also relates to a system for treating at least one symptom of at least one medical condition discussed herein (including any document incorporated herein), wherein the system comprises a vacuum source and/or supply, a housing configured to at least partially receive therein a penis, and a garment or support configured to retain and/or support the housing.

The invention also relates to a method for treating at least one symptom of at least one medical condition discussed herein (including any document incorporated herein), wherein the method comprises creating suction or vacuum in a housing configured to at least partially receive therein a penis, and supporting and/or retaining the housing on the user with a garment or wearable support.

The invention also relates to a method for causing an erection of the penis during sleep using at least one device embodiment as shown and/or described herein.

The invention also relates to a method for causing an erection of the penis during sleep which substantially simulates at least one NPT event. The at least one NPT event may be characterized by the user achieving an erection and maintaining it for between about twenty minutes and about forty minutes.

The invention also relates to a method of treating a loss of or diminishment of NPT events using at least one device embodiment as shown and/or described herein, wherein the method comprises using the device, producing normal and healthy blood flow to the penis such that the penile blood has good or normal oxygenation.

The invention also relates to a method of treating a loss of or diminishment of NPT events using at least one device embodiment as shown and/or described herein, wherein the method comprises using the device, causing several NPT episodes in a user during night-time sleep. The night-time sleep may comprise rapid eye movement (REM) sleep.

The invention also relates to a method of treating a loss of or diminishment of NPT events resulting from ED using at least one device embodiment as shown and/or described herein.

The invention also relates to a method of restoring and/or maintaining penile length of a user having diminished NPT and/or ED using at least one device embodiment as shown and/or described herein. The loss of penile length may be a side-effect of the diminished NPT and/or ED.

The invention also relates to a method of restoring and/or providing normal and healthy blood flow (and/or oxygenation and/or stretching) to the penis and/or which can restore or maintain penile length using at least one device embodiment as shown and/or described herein.

The invention also relates to a method of restoring and/or maintaining penile length of a user having diminished or loss of NPT and/or ED, wherein the method comprises following a surgical procedure, using at least one device embodiment as shown and/or described herein. The surgical procedure may comprise radical retropubic prostatectomy.

The invention also relates to a method of restoring and/or maintaining penile length using at least one device embodiment as shown and/or described herein.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 4 shows a front or outside view a portion of the garment or wearable support shown in FIG. 5;

FIG. 5 shows a side cross-section view of a portion of the garment or wearable support used in the embodiment of FIG. 1;

FIG. 6 shows a rear or inside view a portion of the garment or wearable support shown in FIG. 5;

FIG. 7 shows a side cross-section view of a portion of the garment or wearable support along with a side view of the housing and illustrates one non-limiting way in which the housing can be inserted into a main opening in the garment;

FIG. 9 shows a side partial cross-section view of the housing and shows an inner vacuum area, a vacuum nipple, a main housing, an elbow section, and a flange section having a flange member and a conformable sealing member which can provide a seal to a base portion of the penis;

FIG. 10 shows a side partial cross-section view of another non-limiting embodiment of the housing having a flexible or bendable/accordion section;

FIG. 11 shows a side view of another non-limiting embodiment of the housing having a flexible or bendable section which can assume a generally straight configuration in an initial position;

FIG. 12 shows a side partial cross-section view of the housing shown in FIG. 11;

FIG. 13 shows a front view of the controller shown in FIG. 1 and shows a vacuum supply nipple, a display and control buttons;

FIG. 14 shows a side view of the controller shown in FIG. 13 and shows front and rear housing parts;

FIG. 25 shows a side view of another non-limiting embodiment of a housing or cylinder which can be used with any of the embodiments disclosed herein and includes hook and loop connection sections;

FIG. 26 shows a cross-section view of the housing or cylinder shown in FIG. 25.

FIGS. 27-29 show a sixth non-limiting embodiment of the invention and illustrates a garment or wearable support, a vacuum housing or cylinder is not shown. An electronic device or controller is shown connected to a front panel of the garment via hook and loop attachments so as to eliminate the need to a controller pocket;

FIG. 35A shows an increasing amount of vacuum used at three different time periods, events, or sessions throughout night-time. FIG. 35B shows a steady and shorter amount, e.g., 20 minutes, of vacuum at three different time periods throughout night-time. FIG. 35C shows a steady and longer amount, e.g., 40 minutes, of vacuum used at three different time periods throughout night-time;

FIG. 38 shows another non-limiting embodiment of a cylinder that can be used in accordance with the invention;

FIG. 39 shows the cylinder of FIG. 38 along with a non-limiting embodiment of a sheath which can be used with the cylinder in accordance with the invention;

FIG. 41 shows the cylinder of FIG. 38 with the distal ring member disconnected therefore;

FIG. 42 shows the cylinder of FIG. 40 arranged adjacent the penile opening area of a garment;

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

The following is a description of non-limiting embodiments of a device, system and/or method that therapeutically replicates the normal pattern of nocturnal erectile events of males during sleep, and preferably therapeutically replicates the normal pattern of NPT events of males during REM sleep. One purpose of use of the device is to restore and maintain penile volume in patients who have had disease or surgery that caused a reduction in penile volume from their normal state. Another purpose of the device is treat a loss of or diminishment of NPT events resulting from ED. Still another purpose of the device is to restore and/or maintain penile length, and more specifically, doing so for a user having diminished NPT and/or ED. The loss of penile length can be a side-effect of the diminished NPT and/or ED which can be treated using the device. Still another purpose of the device is to restore and/or provide normal and healthy blood flow (and/or oxygenation and/or stretching) to the penis in a user having, among other things, a loss of or diminishment of NPT events which may or may not be the result of ED. A particularly preferred advantage of the invention relates to using the device to restore and/or maintain penile length of a user having diminished or loss of NPT events and/or ED, wherein, following a surgical procedure, the device is utilized to substantially replicate the NPT events in a predetermined or pre-programmed manner. By way of non-limiting example, the device can be particularly advantageous to treat one or more of the problems noted above, e.g., penile length restoration/maintenance and/or restoring and/or providing normal and healthy blood flow (and/or oxygenation and/or stretching) to the penis, following the procedure; radical retropubic prostatectomy.

Figure 1:
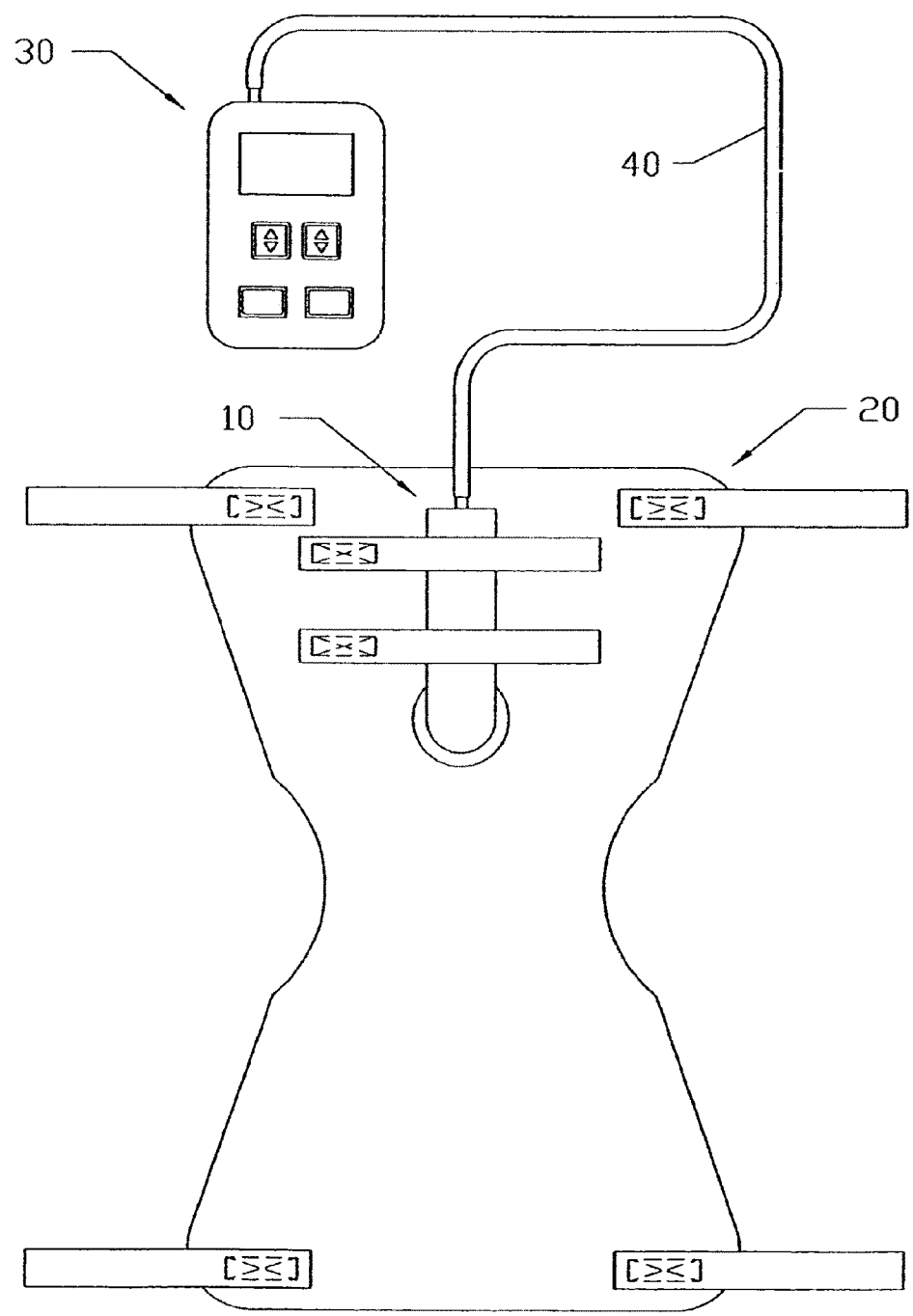
FIG. 1 shows a front view of a first non-limiting embodiment of the invention and illustrates a garment or wearable support, a vacuum housing or cylinder configured to receive therein a human penis, and an electronic device or controller which is capable of being programmed to produce a vacuum condition in the housing at various points in time and for predetermined time periods, and which contains a vacuum or suction pump which can produce a vacuum. A hose or conduit connects the controller to the housing or cylinder.

FIG. 1 shows one non-limiting embodiment of the invention. The device or system is mainly comprised of three parts, a vacuum supply system or controller 30 (that is preferably portable and/or of hand-held size), vacuum cylinder or housing 10, and a garment or wearable support 20 which can take the form of an undergarment to support the vacuum cylinder 10. A hose or tube 40 connects the controller 30 to the vacuum cylinder 10 so as to fluidly connect the controller 30 to the cylinder 10.

The garment, undergarment, or wearable support 20 is preferably capable of supporting the cylinder 10 and can have the shape of, e.g., an adult diaper. Preferably, the garment 20 is made of flexible and comfortable material which can be single layer or multi-layered so as to fit comfortably on the user. Since the user may wear the garment 20 as an undergarment, thereby placing an inside surface next to the user's skin, the garment 20 can preferably utilize a fabric material layer on the inside surface. It would also be advantageous to make the garment 20 washable. By way of non-limiting example, the main portion of the garment 20 can be made of a single or unitary material member. Also by way of non-limiting example, the material can be similar to spandex (elastane) or neoprene. Preferably, the neoprene is covered with a thin nylon material either on one side (smoothskin) or both sides. The main portion of the garment 20 can have generally uniform thickness of between about 1 mm and about 6 mm. Of course, other materials can be utilized provided they can function effectively with the other components used with the garment.

Figure 2:
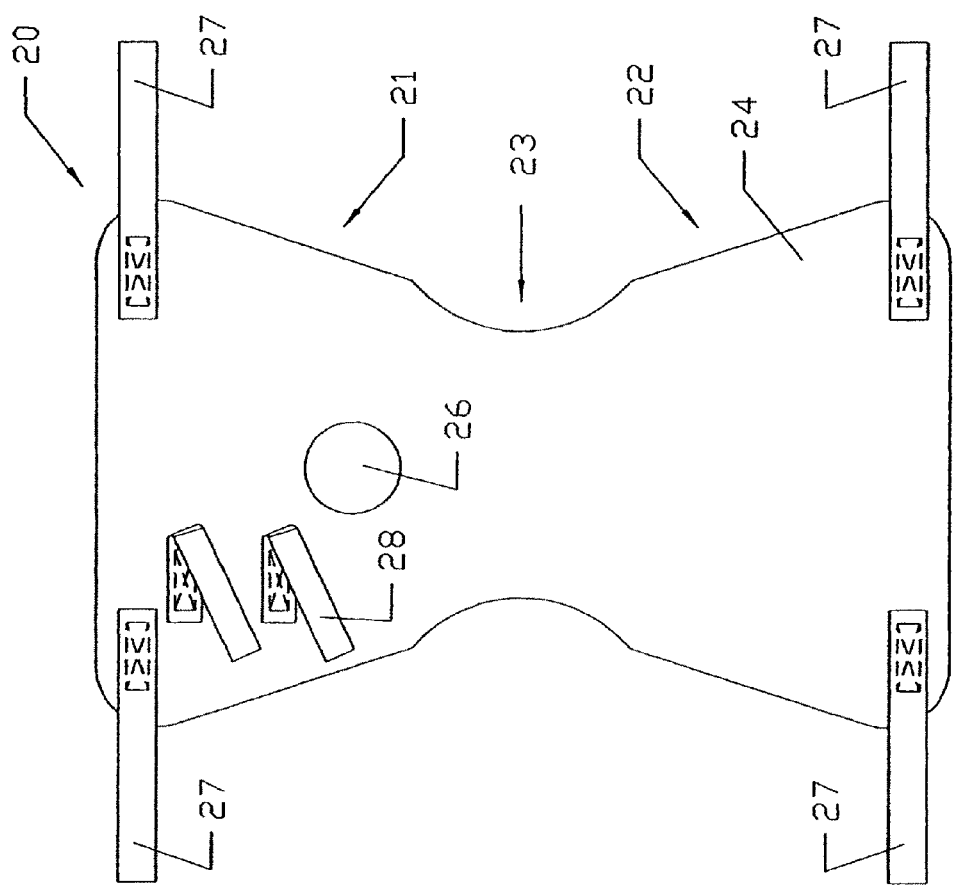
FIG. 2 shows a front or outside view of the garment or wearable support used in the embodiment of FIG. 1. The garment has Velcro® (hook and loop) waist straps, hook and loop housing or cylinder retaining straps, a main opening, a front panel or section configured to at least partially cover a genital area, a central or connecting section, a rear panel or section configured to cover a portion of the buttocks, and a outer surface.
Figure 3:
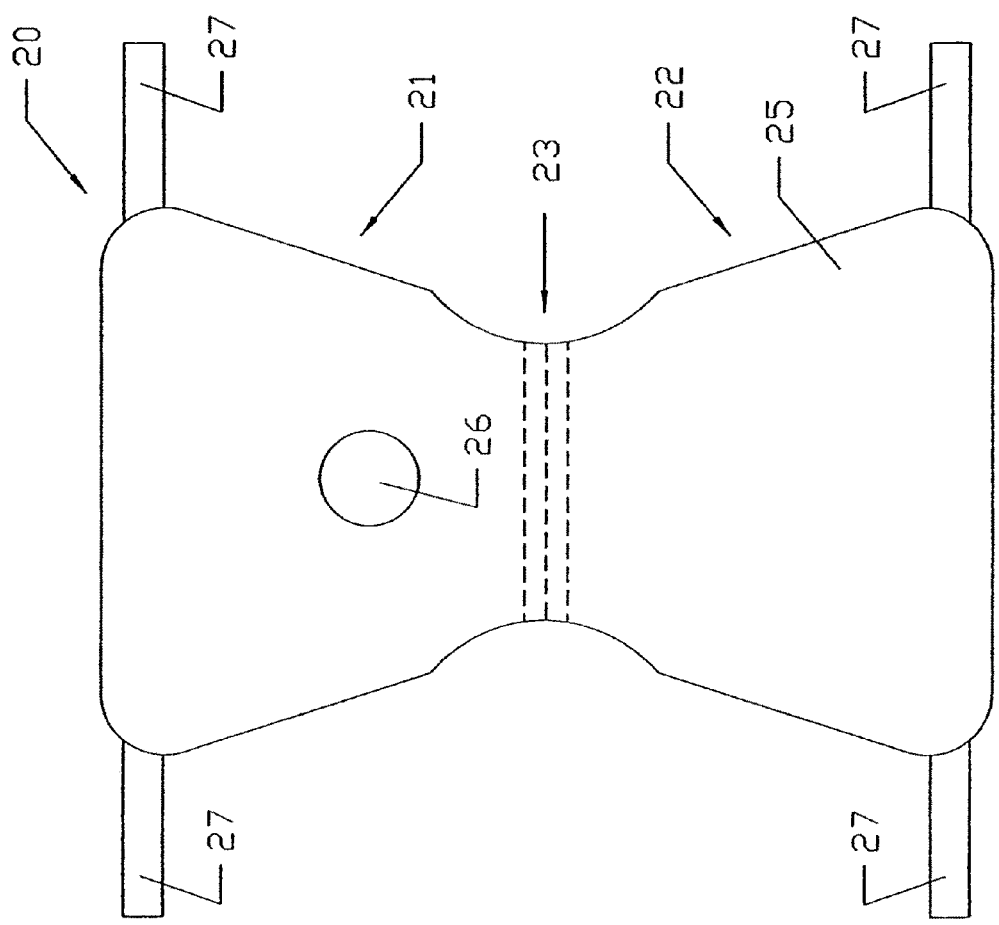
FIG. 3 shows a rear or inside view of the garment or wearable support used in the embodiment of FIG. 1 and further shows an inside surface.

With reference to FIGS. 2-6, it can be seen that the garment 20 has front section 21, a back section 22, and a centrally arranged connecting section 23. The front side section 21 is configured to be placed adjacent to a user's front pelvis or genital area with a top edge being positioned in the general area of the front side of the user's waist. The back side section 22 is configured to be placed adjacent to a user's buttock area with a top edge being positioned in the general area of the back side of the user's waist. The center or connecting section 23 is configured to be placed adjacent to the area between the user's legs (between the genital area and the buttock) and has oppositely arranged inwardly curved areas to comfortably accommodate the insides of the user's legs. The section 23 can also be formed with generally vertically oriented folds or pleats (not shown) to allow the garment 20 to be comfortably worn by different user's, i.e., users of various weights and sizes. Preferably, as shown in FIG. 3, the section 23 has generally horizontal fold or pleat lines (indicated by dashed-lines) which allow the section 23 to bend or conform more easily to the area between a user's legs. A front or outside surface 24 of the garment 20 is defined on the sections 21-23 as is a back or inside surface 25. The inside surface 25 (see FIG. 3) is configured to face or contact the user's skin, and is preferably a surface which can be comfortably placed on the user's skin for at least the period of a user's sleep, e.g., 6 to 10 hours, without causing discomfort or adverse effects to the user's skin. The outside surface 24 (see FIG. 2) is configured to face in an opposite direction from the inside surface 25, and is preferably a surface which can be comfortably placed in contact with the user's outer clothing and/or bedding materials of which this surface may contact. This surface 24 can also be a more durable surface and can contain information or directions on how to use or install the device or system.

Again, with reference to FIG. 2, it can be seen that the garment 20 has upper and lower straps 27. Each strap 27 has one end which is permanently and/or non-removably connected, e.g., via stitching, to the respective sections 21 and 22 and a free end. When the user installs or puts-on the garment 20, the free ends of the upper straps 27 can be connected together in an area of the user's two waist flank areas above the hips. This connection can be effectuated a variety of ways, but is preferably an adjustable and easily releasable connection. Most preferably, the free end of the straps 27 contain hook and loop sections which allow the user to adjust the tension of the straps 27 and makes the garment 20 relatively easy to remove and install on the user. The straps 27 can be made of either a non-stretchable material or a stretchable material to allow for more wider range of adjustment, but are preferably long enough to have their free ends overlap on each side, thereby providing a suitable area for connecting together the straps 27. Although not provided in the embodiment shown in FIG. 1, the garment 20 can also utilize only the top straps 27 (i.e., those of section 21), whereby the free ends of these straps 27 are connectable with hook and loop patches (not shown) arranged in the areas where the lower straps 27 are stitched to the section 22. Alternatively, the garment 20 can utilize only the bottom straps 27 (i.e., those of section 22), whereby the free ends of these straps 27 are connectable with hook and loop patches (not shown) arranged in the areas where the upper straps 27 are stitched to the section 21.

Figure 8:
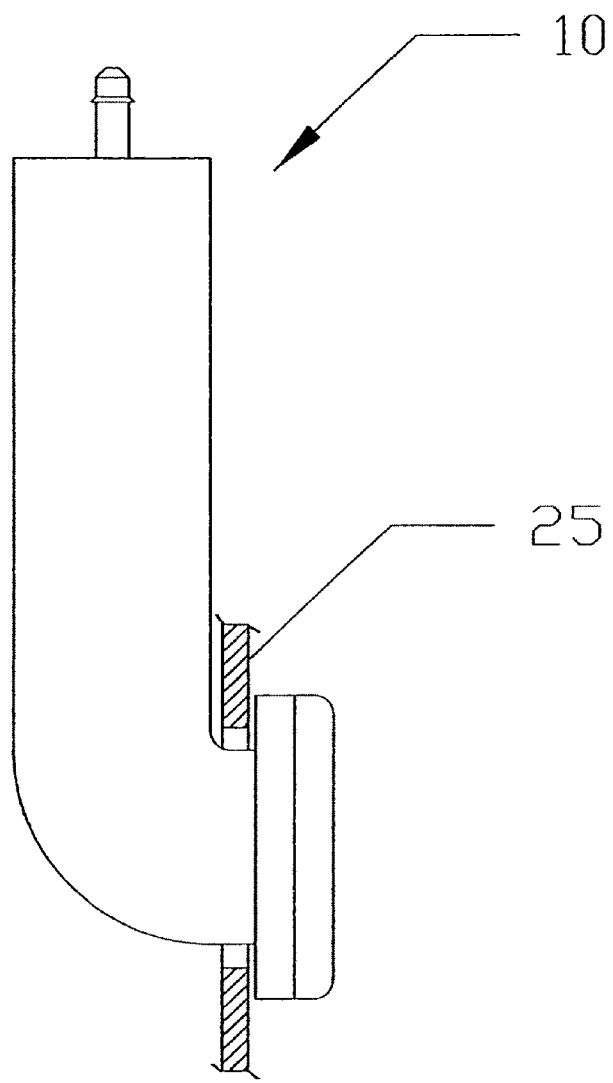
FIG. 8 shows a side cross-section view of a portion of the garment or wearable support along with a side view of the housing and illustrates the housing in an installation position relative to the main opening in the garment.

Again, with reference to FIG. 2, it can be seen that the garment 20 includes a main through opening 26 which is generally located in an area of section 21 of the garment 20 so as to be generally located in an area of the base of the penis. The opening 26 is sized and configured to receive therein the vacuum cylinder 10 (see FIG. 7). The size and shape of the opening 26 in the garment 20 can be substantially equal to the outside diameter of the vacuum cylinder 10 and is also preferably smaller than the outside diameter of the flange section 15 of the cylinder 10 in order to support the cylinder in the general position shown in FIG. 8. The opening area of the section 21 serves to secure the vacuum cylinder 10 in position at the base of the penis. Although not shown, a connection such as, e.g., hook and loop attachment strips, can be used to secure the section 15 of the cylinder 10 to the inside surface 25 around the opening 26.

With reference again to FIG. 2, it can be seen that the garment 20 can utilize one or more additional straps 28. Each strap 28 has one end which is permanently and/or non-removably connected, e.g., via stitching, to section 21 and a free end. The free ends of the straps 28 can be connected to portions of the section 21 on the other side of section from the opening 26 as shown in FIG. 1. This connection can be effectuated a variety of ways, but is preferably an adjustable and easily releasable connection. Most preferably, the free end of the straps 28 contain hook and loop sections which allow the user to adjust the tension of the straps 28 so as to more securely and comfortably secure the cylinder 10 to the garment 20 in the position and/or orientation shown in FIGS. 1 and 8. The straps 28 can be made of either a non-stretchable material or a stretchable material to allow for more wider range of adjustment, but are preferably long enough to have their free ends connect to one or more patches (not shown) of hook and loop on the section 21 on the other side (i.e., right side in FIG. 2) of the opening 26.

With reference to FIG. 9, the vacuum cylinder 10 includes a generally cylindrical section 11 and an elbow section 14. A distal end of the cylinder 10 can be closed except for a small opening arranged in a nipple or hose connector 13. The nipple 13 can be connected to one end of the hose 40 (see FIG. 1) such that when a vacuum suction is created by the controller 30, the hose 40, which has an opposite end connected to the controller 30, draws air out of the cylinder 10 and thereby creates a vacuum in the cylinder 10. This vacuum causes a penis positioned in the cylinder 10 to become erect and/or experience erection. A proximal end of the cylinder 10 includes a flange section 15. As explained above, the flange section 15 is configured to abut and/or be supported by the opening 26 of the garment 20. The flange section 15 can preferably utilize a relatively soft, low durometer deformable material forming member 17, such as, e.g., silicone or neoprene, that will conform to the skin at the base of the penis and form a seal. Preferably, the member 17 can be non-removably and/or permanently attached to the flange section 16 via, e.g., adhesive bonding. Alternatively, the member 17 may be made removable from the flange 16 by using a releasable snap connection. In this latter case, care should be taken to ensure that there is no vacuum leakage between section 16 and member 17. The member 17 of the vacuum cylinder 10 can preferably be an annulus shaped member with an inside diameter at least slightly smaller than an inside diameter (ID) of the vacuum cylinder 10, and an outer diameter (OD) that is somewhat larger than the OD of the vacuum cylinder 10, i.e., having an OD about the same size as the OD of the flange 16. The flange section 15 can thereby form a soft base which, when placed in contact with the skin at the base of the penis, ensures a comfortable fit to the user and provides secure vacuum seal to the penis. The cylinder 10 can also be made in various sizes to accommodate various ranges of penis length and girth. In this regard, the flange section 15 can also be varied to properly seal to penises which range in girth. As such, system may come equipped or packaged with the garment 20, the controller, the house, and plural cylinders 10 of different sizes. The user can then select the proper cylinder 10 and position it on the garment 20 for use. The invention also contemplates using substances to perfect a vacuum seal between the flange section 15 and the user's penis such as, e.g., K-Y gel or a similar gel. Such substances can also make it easier to install and remove the penis from the cylinder 10. By way of non-limiting example, the cylinder 10 can be made of a synthetic resin material similar to the materials currently being used to create penile erections.

With reference to FIG. 10, there is shown another non-limiting embodiment of the vacuum cylinder 10' which can be utilized with any of the systems disclosed herein. The cylinder 10' is substantially similar to that of FIG. 9, except that it utilizes an elbow section 14' having the form of an accordion and which is flexible in the sense that the angle between an axis of section 11 and section 15 can change.

With reference to FIGS. 11 and 12, there is shown still another non-limiting embodiment of the vacuum cylinder 10" which can be utilized with any of the systems disclosed herein. The cylinder 10" is substantially similar to that of FIG. 10, except that the elbow section 14" is sufficiently flexible so that flange section 15" can assume either and both of the positions shown in FIG. 11 (straight position) and FIG. 10 (bent position), as well as any angular position there between. This embodiment allows the user to install the cylinder 10" over the penis (while in the position shown in FIG. 11) before the cylinder 10" and penis are passed through the opening 26 of the garment 20 (in a manner similar to that shown in FIG. 7) and then bent into the position shown in FIGS. 8 and 10.

Figure 15:
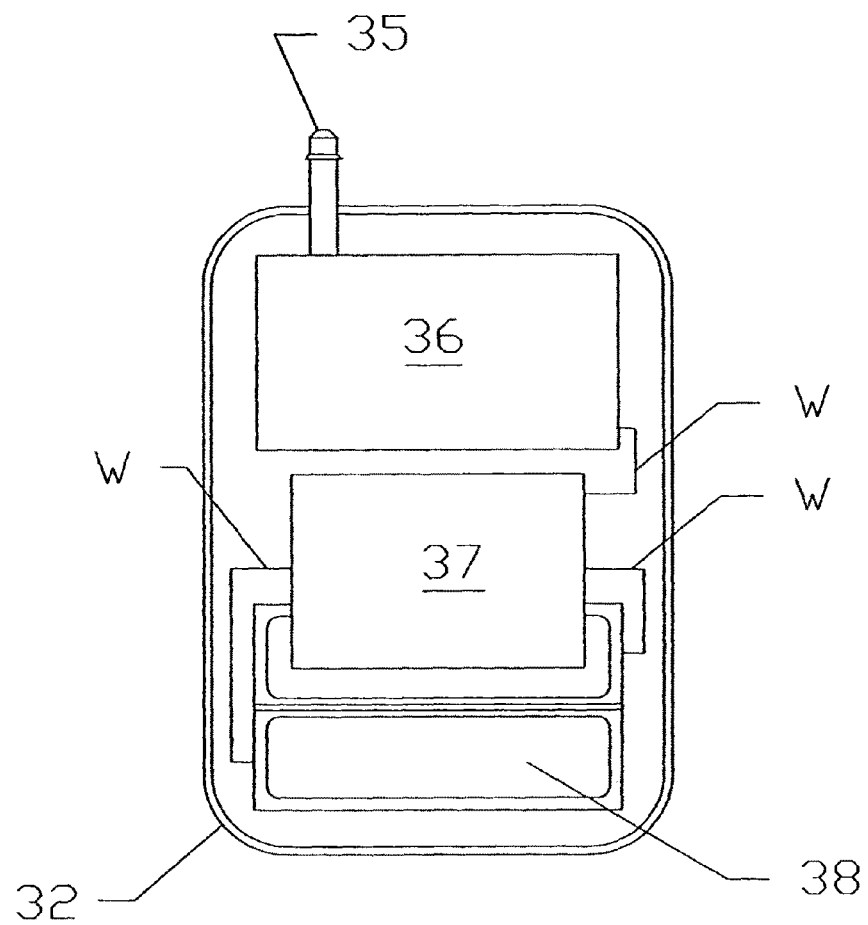
FIG. 15 shows an inside view of the controller shown in FIG. 13 and shows a vacuum pump, a circuit board, a power supply or batteries, and electrical wires.

With reference to FIGS. 13-15, the controller 30 includes housing parts 31 and 32, a display 33, various control buttons 34, a nipple 35 which connects the vacuum source or suction pump 36 arranged in the controller 30 to a hose 40, a circuit board 37, and a power supply which can have the form of batteries 38. Wires W are utilized to connect the batteries 38 to the circuit board 37 and the circuit board 37 to the suction pump 36. The device 36 produces a vacuum or suction which, via hose 40, draws air from the cylinder 10, thereby creating vacuum suction in the cylinder 10. In the embodiment shown in FIG. 1, the controller 30 can be arranged remote from the user but, whose suction can be communicated via the hose 40 to the cylinder 10.

Preferably, the controller 30 is programmable and/or is otherwise capable of producing suction for one or more predetermined time periods and at one or more predetermined points in time. This can include an essentially unlimited number of operating modes, but is preferably similar to normal or natural NPT events. Thus, for example, the controller 30 is preferably capable of being programmed so as to cause suction at a first predetermined level, for a first predetermined time period, and at a first predetermined start time (preferably occurring during REM sleep). This will cause the penis to assume a first nighttime erection. Then, the controller 30 can turn off the suction for a predetermined time period and at a predetermined time, thereby allowing the penis to relax. Thereafter, the controller 30 can cause suction again at a second predetermined level, for a second predetermined time period, and at a second predetermined start time (again preferably occurring during REM sleep). This will cause the penis to assume a second nighttime erection. Then, the controller 30 can turn off the suction for a predetermined time period and at a predetermined time. Thereafter, the controller 30 can cause suction again at a third predetermined level, for a third predetermined time period, and at a third predetermined start time (again preferably occurring during REM sleep). This will cause the penis to assume a third nighttime erection. If a typical male experiences three NPT events during REM sleep each night, the program sequence noted above can be said to simulate normal or natural NPT events. The first, second and third suction levels can be controlled and varied as desired based on values which are input or programmed into the controller 30 via the buttons 34. Similarly, the first, second and third start times can be controlled and varied as desired based on values which are input or programmed into the controller 30 via the buttons 34. Finally, the first, second and third time periods can be controlled and varied as desired based on values which are input or programmed into the controller 30 via the buttons 34. Such values can be determined in a number of possible ways such as, e.g., empirically for a range of users based on a common diagnosis, tailored to a particular user as necessary, and/or modified or changed over a series of nights in order to prevent injury to the user and/or provide a transition period between partial NPT events and full NPT events. In order to provide this programming capability, the circuit board 37 preferably includes electronics which include, among other things, proprietary firmware, one or more timers, switches, and vacuum level controls.

Figure 16:
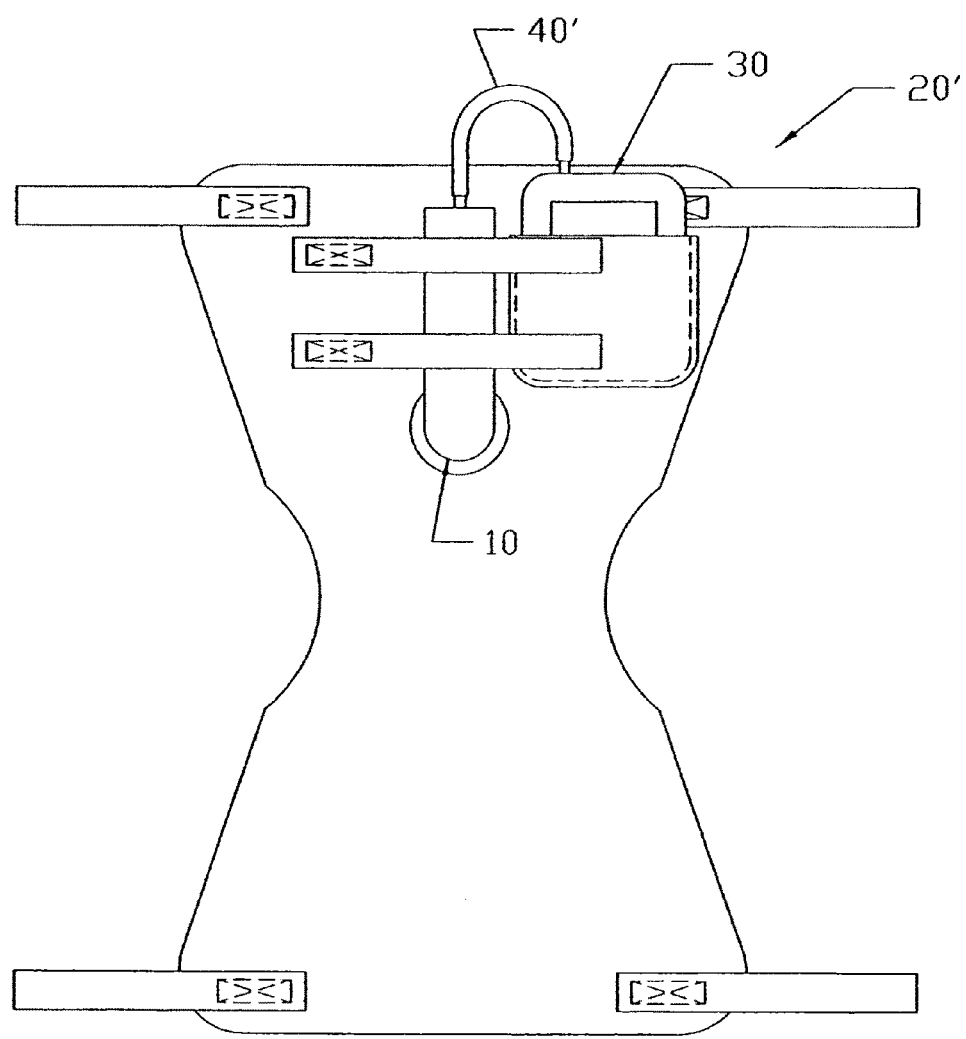
FIG. 16 shows a front view of a second non-limiting embodiment of the invention and illustrates a garment or wearable support, a vacuum housing configured to receive therein a human penis, and an electronic device or controller which is capable of being programmed to produce a vacuum condition in the housing at various points in time and for predetermined time periods, and contains a vacuum pump which can produce a vacuum. A hose or conduit connects the controller to the housing.

FIG. 16 shows another non-limiting embodiment of the invention. The device or system, like that of FIG. 1, is mainly comprised of three parts, a controller 30, vacuum cylinder or housing 10, and a garment or wearable support 20' which can take the form of an undergarment to support the vacuum cylinder 10. A short hose or tube 40' connects the controller 30 to the vacuum cylinder 10. However, unlike the embodiment of FIG. 1 which utilizes a controller 30 which can be arranged remote from the garment 20 and the user, the embodiment shown in FIG. 16 places the controller 30 on the garment 20' and therefore on the user.

As in the previous embodiment, the garment, undergarment, or wearable support 20' is preferably capable of supporting the cylinder 10 and can have the shape of, e.g., an adult diaper. Preferably, the garment 20' is made of flexible and comfortable material which can be single layer or multi-layered so as to fit comfortably on the user. Since the user may wear the garment 20' as an undergarment, thereby placing an inside surface next to the user's skin, the garment 20' can preferably utilize a fabric material layer on the inside surface. As in the previous embodiment, it would also be advantageous to make the garment 20' washable. By way of non-limiting example, the main portion of the garment 20' can be made of a single or unitary material member. Also by way of non-limiting example, the material can be similar to spandex (elastane) or neoprene. Preferably, the neoprene is covered with a thin nylon material either on one side (smoothskin) or both sides. The main portion of the garment 20' can have generally uniform thickness of between about 1 mm and about 6 mm. Of course, other materials can be utilized provided they can function effectively with the other components used with the garment.

Figure 17:
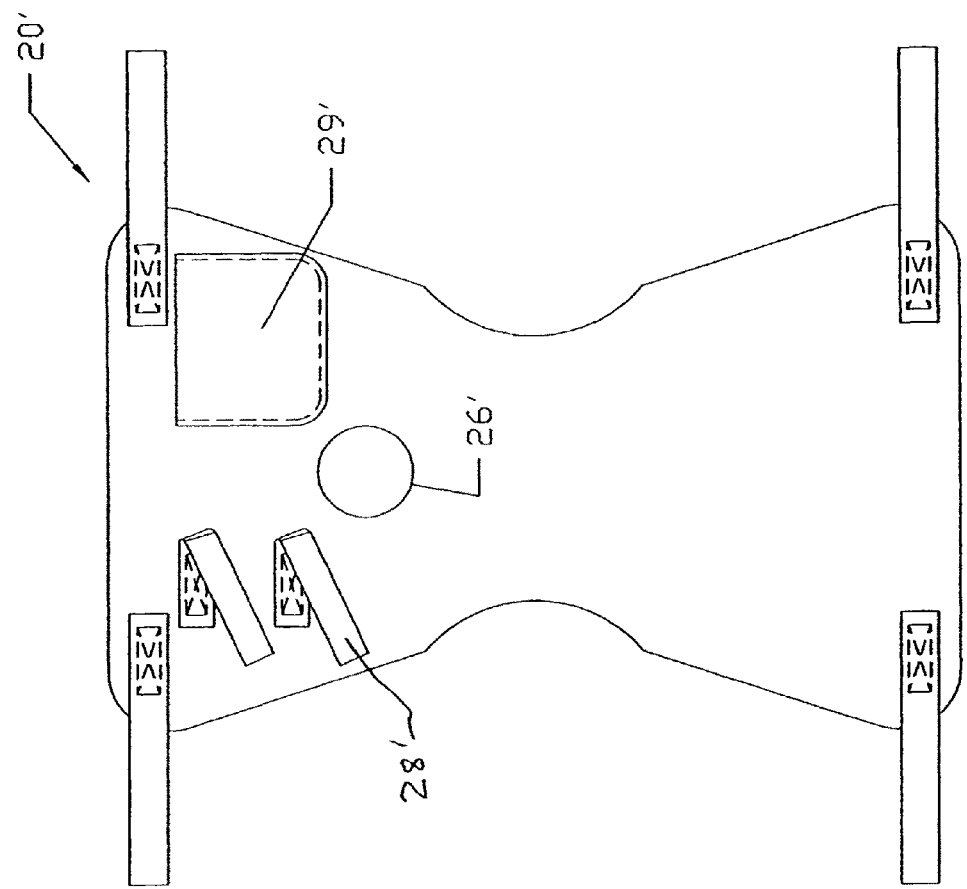
FIG. 17 shows a front or outside view of the garment or wearable support used in the embodiment of FIG. 16. The garment has hook and loop waist straps, hook and loop housing retaining straps, a main opening, a front panel configured to at least partially cover a genital area, a central area, a rear panel configured to cover a portion of the buttocks, as well as a pocket which can receive therein the controller.
Figure 18:
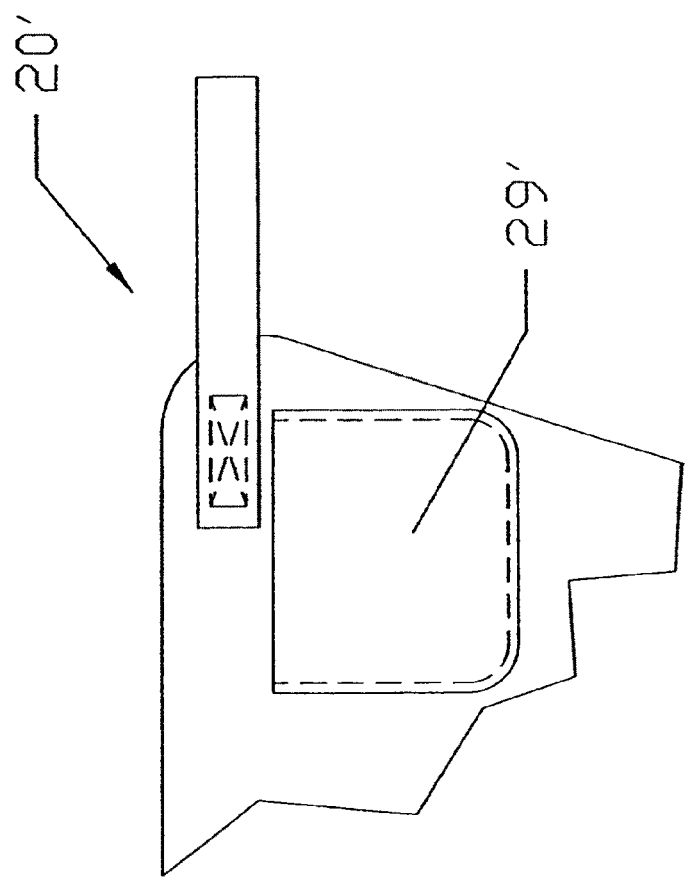
FIG. 18 shows an enlarged partial side view of the pocket which can receive therein the controller shown in FIG. 17.
Figure 19:
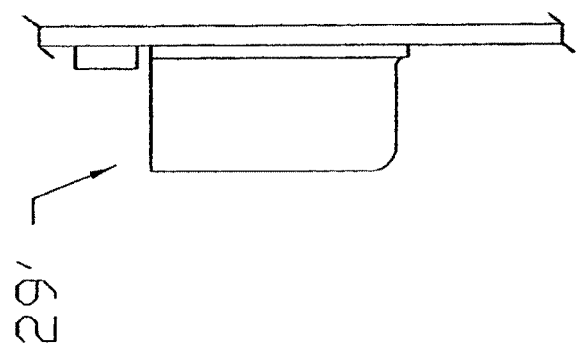
FIG. 19 shows a front view of the pocket shown in FIG. 18.

With reference to FIGS. 17-19, it can be seen that the garment 20' has front side section, a backside section, and a centrally arranged connecting section as in the previous embodiment. The front side section is configured to be placed adjacent to a user's front pelvis or genital area with a top edge being positioned in the general area of the front side of the user's waist. The back side section is configured to be placed adjacent to a user's buttock area with a top edge being positioned in the general area of the back side of the user's waist. The center or connecting section is configured to be placed adjacent to the area between the user's legs (between the genital area and the buttock) and has oppositely arranged inwardly curved areas to comfortably accommodate the insides of the user's legs. The connecting section can also be formed with generally vertically oriented folds or pleats (not shown) to allow the garment 20' to be comfortably worn by different user's, i.e., users of various weights and sizes. Preferably, the connecting section has generally horizontal fold or pleat lines (similar to the dashed-lines in FIG. 3) which allow the center section to bend or conform more easily to the area between a user's legs. The inside surface is configured to face or contact the user's skin, and is preferably a surface which can be comfortably placed on the user's skin for at least the period of a user's sleep, e.g., 6 to 10 hours, without causing discomfort or adverse effects to the user's skin. The outside surface is configured to face in an opposite direction from the inside surface, and is preferably a surface which can be comfortably placed in contact with the user's outer clothing and/or bedding materials of which this surface may contact. This surface can also be a more durable surface and can contain information or directions on how to use or install the device or system.

Again, with reference to FIG. 17, it can be seen that the garment 20', similar to the embodiment shown in FIG. 1, has upper and lower straps. Each strap has one end which is permanently and/or non-removably connected, e.g., via stitching, to the respective sections front and back sections and a free end. When the user installs or puts-on the garment 20', the free ends of the upper straps can be connected together in an area of the user's two waist flank areas above the hips. This connection can be effectuated a variety of ways, but is preferably an adjustable and easily releasable connection. Most preferably, the free end of the straps contain hook and loop sections which allow the user to adjust the tension of the straps and makes the garment 20' relatively easy to remove and install on the user. The straps can be made of either a non-stretchable material or a stretchable material to allow for more wider range of adjustment, but are preferably long enough to have their free ends overlap on each side, thereby providing a suitable area for connecting together the straps. Although not provided in the embodiment shown in FIG. 17, the garment 20' can also utilize only the top straps (i.e., those of the front section), whereby the free ends of these straps are connectable with hook and loop patches (not shown) arranged in the areas where the lower straps are stitched to the back section. Alternatively, the garment 20' can utilize only the bottom straps (i.e., those of back section), whereby the free ends of these straps are connectable with hook and loop patches (not shown) arranged in the areas where the upper straps are stitched to the front section.

Again, with reference to FIG. 17, it can be seen that the garment 20' includes, like the embodiment of FIG. 1, a main through opening 26' which is generally located in an area of front section of the garment 20' so as to be generally located in an area of the base of the penis. The opening 26' is sized and configured to receive therein the vacuum cylinder 10 (see, e.g., FIG. 7). The size and shape of the opening 26' in the garment 20' can be substantially equal to the outside diameter of the vacuum cylinder 10 and is also preferably smaller than the outside diameter of the flange section 15 of the cylinder 10 in order to support the cylinder in the general position shown in FIG. 8. The opening area of the front section serves to secure the vacuum cylinder 10 in position at the base of the penis. Although not shown, a connection such as, e.g., hook and loop attachment strips, can be used to secure the section 15 of the cylinder 10 to the inside surface around the opening 26'.

With reference again to FIG. 17, it can be seen that the garment 20' can utilize one or more additional straps 28'. Each strap 28' has one end which is permanently and/or non-removably connected, e.g., via stitching, to front section and a free end. The free ends of the straps 28' can be connected to portions of a pocket 29' (see FIG. 16). This connection can be effectuated a variety of ways, but is preferably an adjustable and easily releasable connection. Most preferably, the free end of the straps 28' contain hook and loop sections which allow the user to adjust the tension of the straps 28' so as to more securely and comfortably secure the cylinder 10 to the garment 20' in the position and/or orientation shown in FIG. 16. The straps 28' can be made of either a non-stretchable material or a stretchable material to allow for more wider range of adjustment, but are preferably long enough to have their free ends connect to one or more patches (not shown) of hook and loop on the front section on the other side (i.e., right side in FIG. 17) of the opening 26'. The pocket 29' is sized and configured to receive therein the controller 30 and thus has three sides which are permanently and/or non-removably connected, e.g., via stitching, to the front section, as well as an open upper side (see FIG. 19) which receives therein the controller 30.

Figure 20:
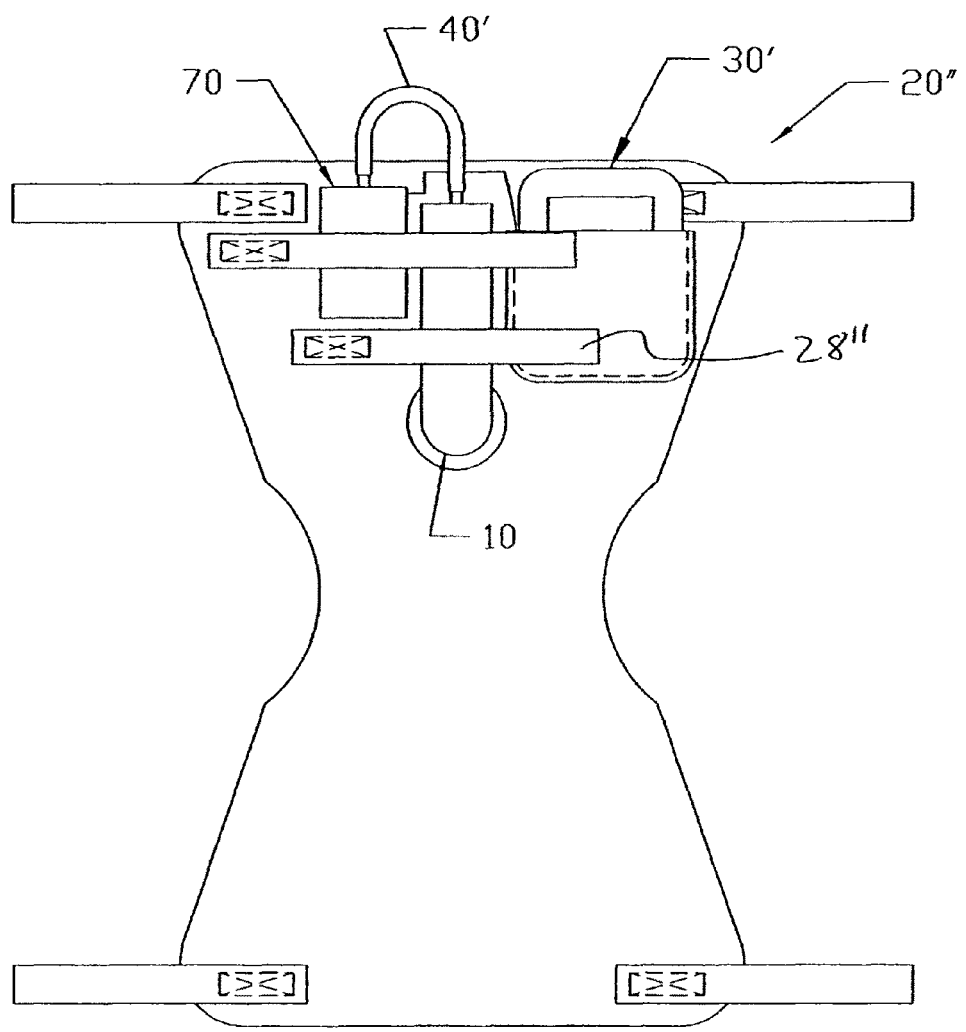
FIG. 20 shows a front view of a third non-limiting embodiment of the invention and illustrates a garment or wearable support, a vacuum housing configured to receive therein a human penis, and an electronic device or controller which is capable of being programmed to produce a vacuum condition in the housing at various points in time and for predetermined time periods, and controls a vacuum pump which can produce a vacuum. A hose or conduit connects the vacuum pump to the housing or cylinder.
Figure 21:
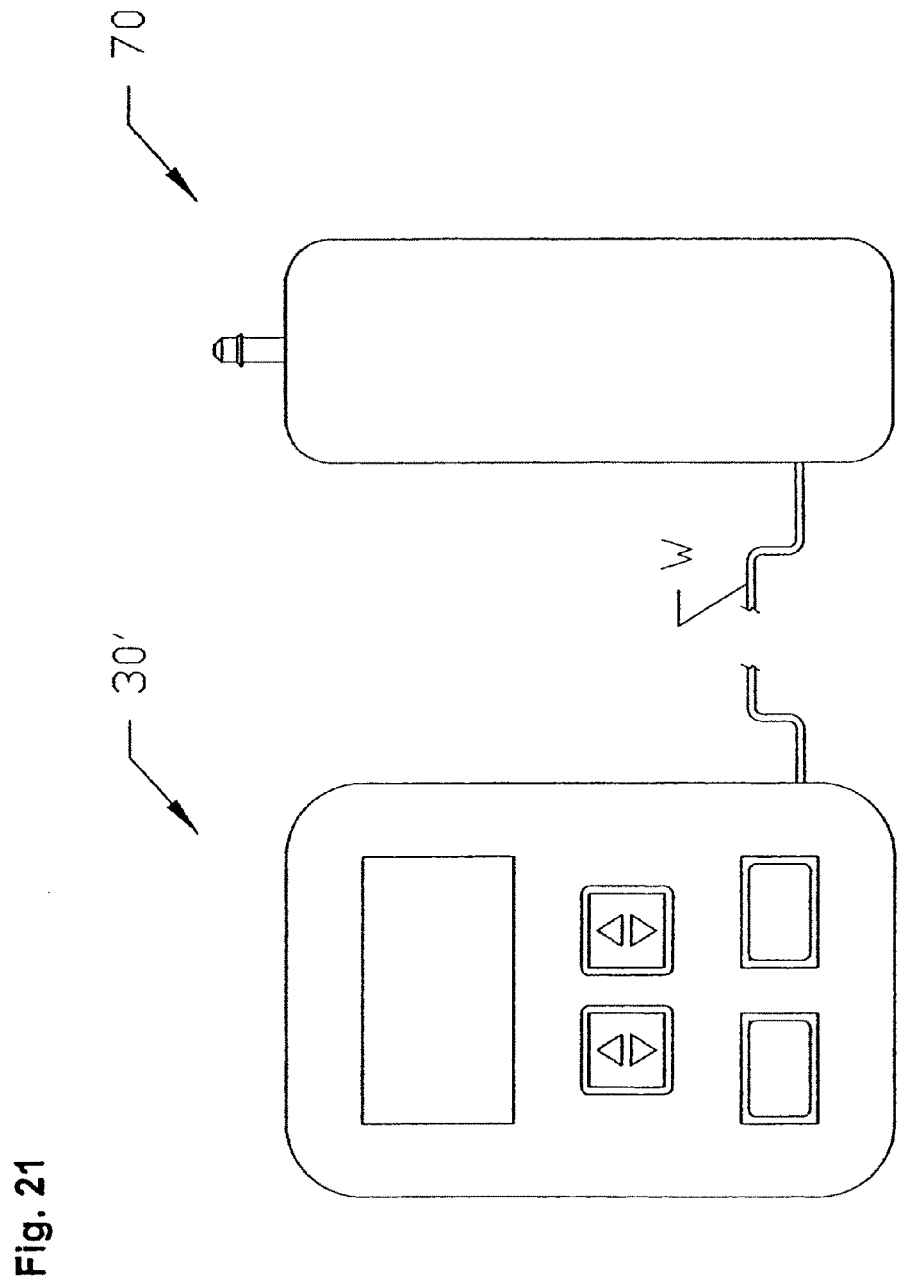
FIG. 21 shows a front view of the controller and vacuum pump shown in FIG. 20 and shows an electrical wire connecting the controller to the vacuum pump.

FIG. 20 shows another non-limiting embodiment of the invention. The device or system is mainly comprised of four parts, a controller 30', a suction pump 70, a vacuum cylinder or housing 10, a garment or wearable support 20" which can take the form of an undergarment to support the vacuum cylinder 10. A short hose or tube 40' connects the suction pump 70 to the vacuum cylinder 10. A wire W connects the controller 30' to the suction pump 70 (see FIG. 21). However, unlike the embodiments of FIG. 16, which utilizes a controller 30 having an internal suction pump, the embodiment shown in FIG. 20 places a separate controller 30' and suction pump 70 on the garment 20".

As in the previous embodiments, the garment, undergarment, or wearable support 20" is preferably capable of supporting the cylinder 10 and can have the shape of, e.g., an adult diaper. Preferably, the garment 20" is made of flexible and comfortable material which can be single layer or multi-layered so as to fit comfortably on the user. Since the user may wear the garment 20" as an undergarment, thereby placing an inside surface next to the user's skin, the garment 20' can preferably utilize a fabric material layer on the inside surface. As in the previous embodiments, it would also be advantageous to make the garment 20" washable. By way of non-limiting example, the main portion of the garment 20" can be made of a single or unitary material member. Also by way of non-limiting example, the material can be similar to spandex (elastane) or neoprene. Preferably, the neoprene is covered with a thin nylon material either on one side (smoothskin) or both sides. The main portion of the garment 20" can have generally uniform thickness of between about 1 mm and about 6 mm. Of course, other materials can be utilized provided they can function effectively with the other components used with the garment.

Again, with reference to FIG. 20 it can be seen that the garment 20" has front side section, a backside section, and a centrally arranged connecting section as in the previous embodiment. The front side section is configured to be placed adjacent to a user's front pelvis or genital area with a top edge being positioned in the general area of the front side of the user's waist. The back side section is configured to be placed adjacent to a user's buttock area with a top edge being positioned in the general area of the back side of the user's waist. The center or connecting section is configured to be placed adjacent to the area between the user's legs (between the genital area and the buttock) and has oppositely arranged inwardly curved areas to comfortably accommodate the insides of the user's legs. The connecting section can also be formed with generally vertically oriented folds or pleats (not shown) to allow the garment 20" to be comfortably worn by different user's, i.e., users of various weights and sizes. Preferably, the connecting section has generally horizontal fold or pleat lines (similar to the dashed-lines in FIG. 3) which allow the center section to bend or conform more easily to the area between a user's legs. The inside surface is configured to face or contact the user's skin, and is preferably a surface which can be comfortably placed on the user's skin for at least the period of a user's sleep, e.g., 6 to 10 hours, without causing discomfort or adverse effects to the user's skin. The outside surface is configured to face in an opposite direction from the inside surface, and is preferably a surface which can be comfortably placed in contact with the user's outer clothing and/or bedding materials of which this surface may contact. This surface can also be a more durable surface and can contain information or directions on how to use or install the device or system.

Again, with reference to FIG. 20, it can be seen that the garment 20", similar to the embodiment shown in FIGS. 1 and 16, has upper and lower straps. Each strap has one end which is permanently and/or non-removably connected, e.g., via stitching, to the respective sections front and back sections and a free end. When the user installs or puts-on the garment 20', the free ends of the upper straps can be connected together in an area of the user's two waist flank areas above the hips. This connection can be effectuated a variety of ways, but is preferably an adjustable and easily releasable connection. Most preferably, the free end of the straps contain hook and loop sections which allow the user to adjust the tension of the straps and makes the garment 20" relatively easy to remove and install on the user. The straps can be made of either a non-stretchable material or a stretchable material to allow for more wider range of adjustment, but are preferably long enough to have their free ends overlap on each side, thereby providing a suitable area for connecting together the straps. Although not provided in the embodiment shown in FIG. 20, the garment 20" can also utilize only the top straps (i.e., those of the front section), whereby the free ends of these straps are connectable with hook and loop patches (not shown) arranged in the areas where the lower straps are stitched to the back section. Alternatively, the garment 20" can utilize only the bottom straps (i.e., those of back section), whereby the free ends of these straps are connectable with hook and loop patches (not shown) arranged in the areas where the upper straps are stitched to the front section.

Again, with reference to FIG. 20 it can be seen that the garment 20" includes, like the embodiment of FIGS. 1 and 16, a main through opening which is generally located in an area of front section of the garment 20" so as to be generally located in an area of the base of the penis. The opening is sized and configured to receive therein the vacuum cylinder 10 (see, e.g., FIG. 7). The size and shape of the opening in the garment 20" can be substantially equal to the outside diameter of the vacuum cylinder 10 and is also preferably smaller than the outside diameter of the flange section 15 of the cylinder 10 in order to support the cylinder in the general position shown in FIG. 8. The opening area of the front section serves to secure the vacuum cylinder 10 in position at the base of the penis. Although not shown, a connection such as, e.g., hook and loop attachment strips, can be used to secure the section 15 of the cylinder 10 to the inside surface around the opening.

With reference again to FIG. 20, it can be seen that the garment 20" can utilize one or more additional straps 28". Each strap 28" has one end which is permanently and/or non-removably connected, e.g., via stitching, to front section and a free end. The free end of the lower strap 28" can be connected to a lower portion of a pocket as shown in FIG. 20. The free end of the upper longer strap 28" can be connected to an upper portion of a pocket as shown in FIG. 20. These connections can be effectuated a variety of ways, but is preferably an adjustable and easily releasable connection. Most preferably, the free end of each strap 28" contains hook and loop sections which allow the user to adjust the tension of the straps 28" so as to more securely and comfortably secure the cylinder 10 and suction pump 70 to the garment 20" in the position and/or orientation shown in FIG. 20. The straps 28" can be made of either a non-stretchable material or a stretchable material to allow for more wider range of adjustment, but are preferably long enough to have their free ends connect to one or more patches (not shown) of hook and loop on the front section on the other side (i.e., right side in FIG. 20) of the opening. As in the embodiment of FIG. 16, the pocket of the embodiment shown in FIG. 20 is sized and configured to receive therein the controller 30', and thus has three sides which are permanently and/or non-removably connected, e.g., via stitching, to the front section, as well as an open upper side which receives therein the controller 30'.

Figure 22:
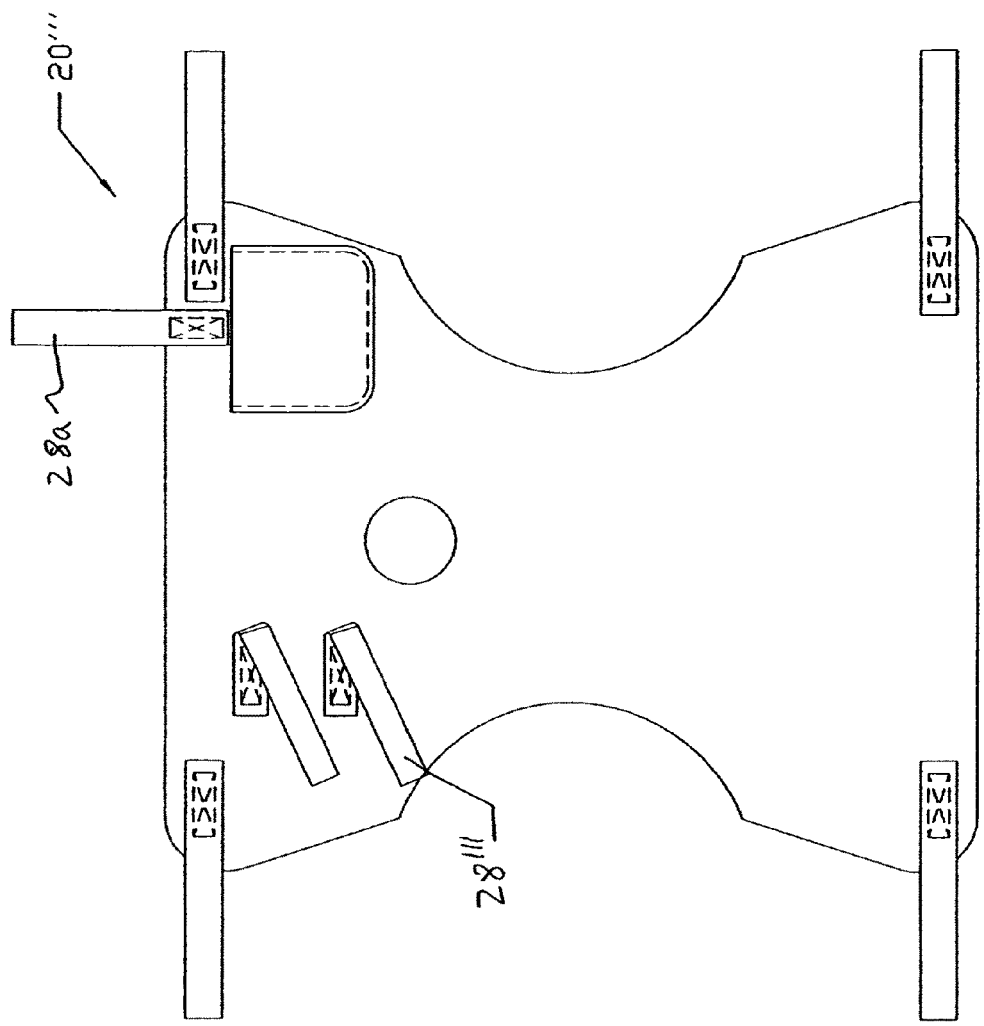
FIG. 22 shows a front or outside view of the garment or wearable support used in a fourth non-limiting embodiment. The garment has hook and loop waist straps, hook and loop housing retaining straps, a main opening, a wider front panel configured to at least partially cover a genital area, a wider central area, a wider rear panel configured to cover a portion of the buttocks, as well as a hook and loop strap which retains the controller in the controller pocket.

With reference to FIG. 22, there is shown another embodiment of the device or system with the cylinder 10, controller 30, and hose 40 removed. This embodiment is similar to that of FIG. 16 except that the front and back sections are wider so that the free ends of the straps 28''' can be connected to hook and loop patches (not shown) of the front section instead of to the pocket as was the case in FIG. 16. The garment 20''' also utilizes a hook and loop strap 28a to ensure that the controller 30 remains securely positioned in the pocket. This strap 28a can also be utilized on the embodiment shown in FIG. 16. This embodiment can otherwise utilize the same materials and features of previous embodiments.

Figure 23:
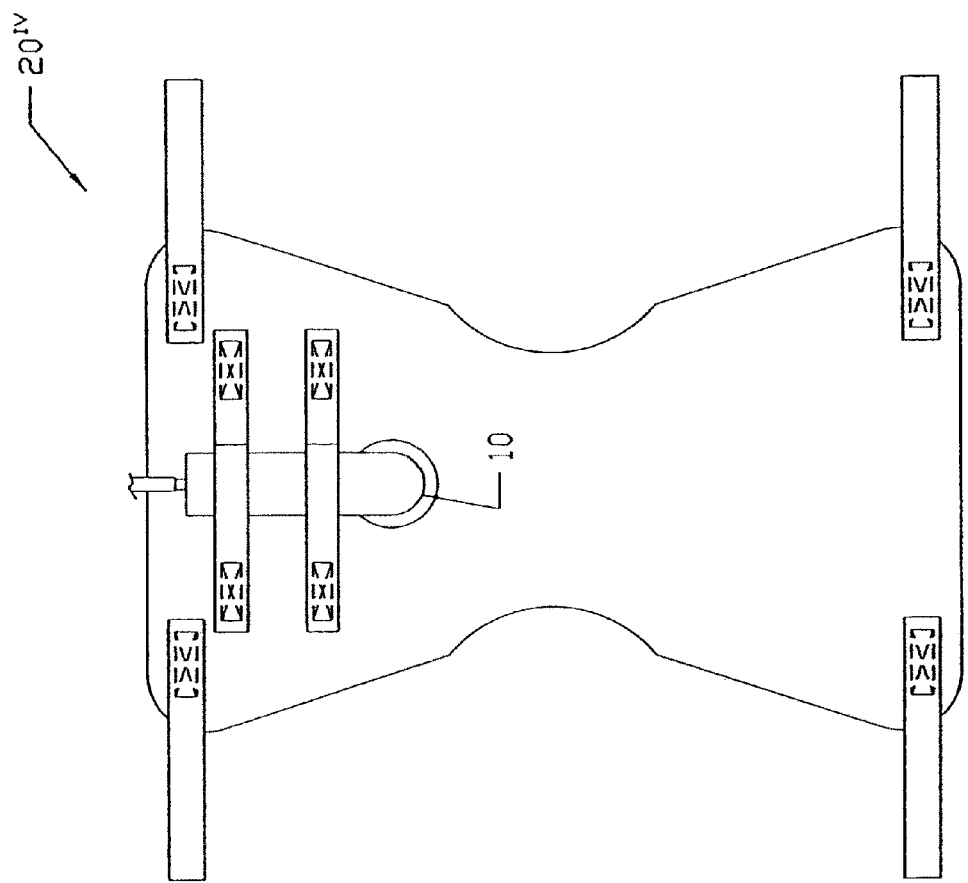
FIG. 23 shows a front view of a fifth non-limiting embodiment of the invention and illustrates a garment or wearable support and a vacuum housing configured to receive therein a human penis. Opposing straps are used to secure the housing in position. An electronic device or controller and/or vacuum source could be of the conventional type and can be positioned within, e.g., a few feet of the user wearing the system shown in FIG. 23. A hose or conduit connects the vacuum pump to the housing or cylinder.
Figure 24:
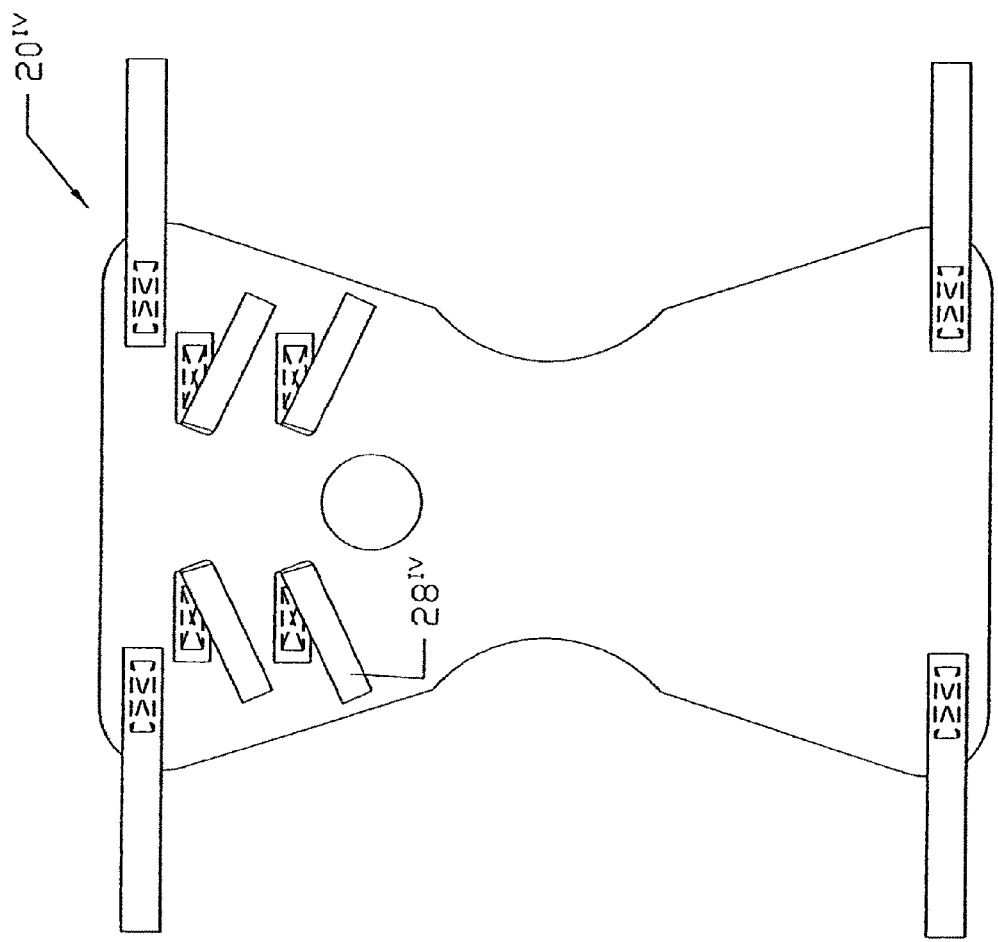
FIG. 24 shows a front view of the garment or wearable support shown in FIG. 23 and illustrates the opposing hook and loop straps.

With reference to FIGS. 23 and 24, there is shown another embodiment of the device or system with the controller 30 removed. This embodiment is similar to that of FIG. 1 except that the front section of the garment $20^{IV}$ utilizes oppositely arranged straps $28^{IV}$ can be connected to each other over the cylinder 10. This embodiment can otherwise utilize the same materials and features of previous embodiments such as that of FIG. 1.

FIGS. 25 and 26 show another non-limiting embodiment of the cylinder 10''' which can be utilized with any of the embodiments disclosed herein. The cylinder 10''' includes one or more hook and loop connection sections or patches 18''' which can be connected to the additional straps 28, 28', 28", 28''' and $28^{IV}$, so as to prevent or limit lateral movement of the cylinder 10 relative to the garment 20.

Figure 27:
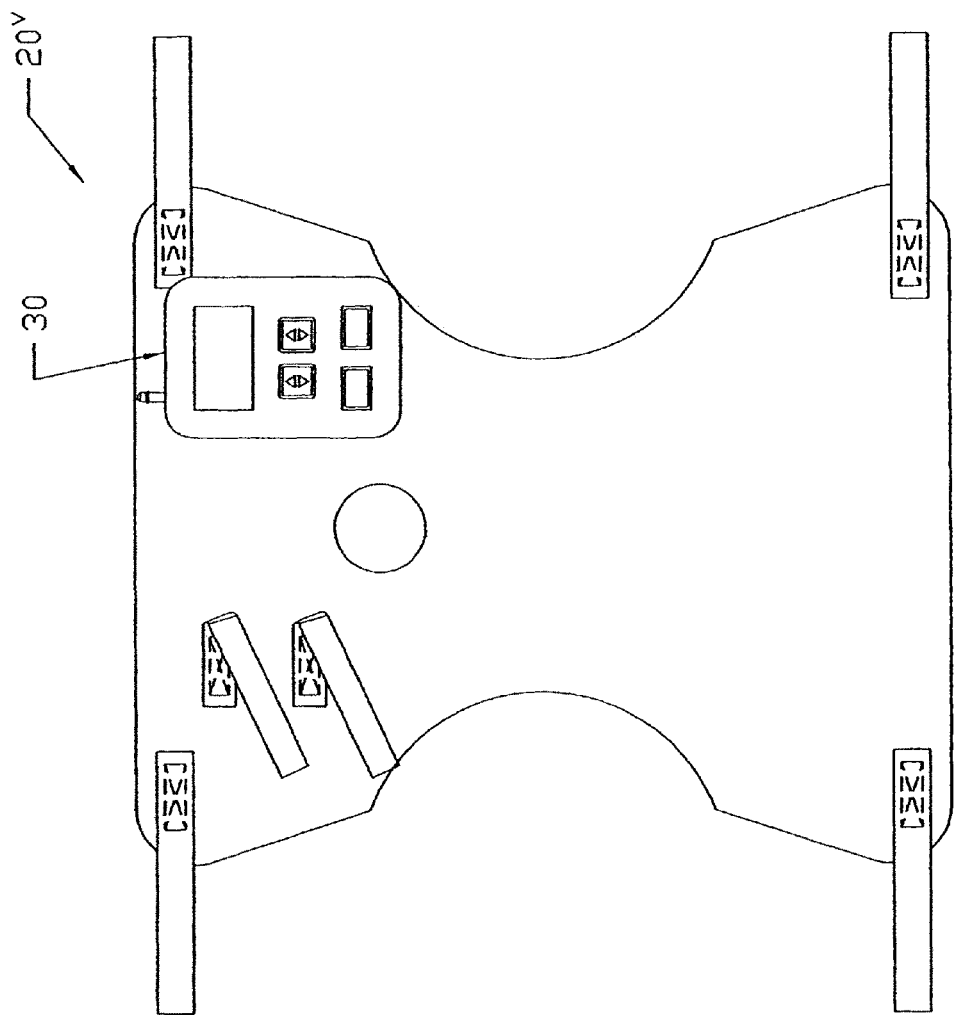

With reference to FIGS. 27-29, there is shown another embodiment of the device or system with the cylinder 10 and hose 40 removed. This embodiment is similar to that of FIG. 1 except that the front and back sections are wider so that the free ends of the cylinder securing straps can be connected to hook and loop patches (not shown) of the front section, and except that the front section includes a hook and loop patch 50A which can be connected to another hook and loop patch 50B arranged on a rear side of the controller 30. This eliminates the need for a pocket on the garment to retain the controller. Although not shown, the embodiment shown 20 can be modified so that the suction pump 70 and controller 30 are each secured to the front section of the garment using similar hook and loop patches. This embodiment can otherwise utilize the same materials and features of previous embodiments.

Figure 30:
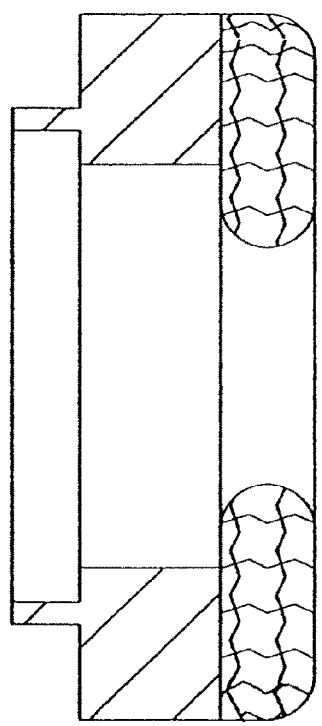
FIG. 30 shows a cross-section view of a flange section of a non-limiting embodiment of the housing or cylinder. The flange section is configured to be removable from the main portion of the housing or cylinder. The invention contemplates utilizing a number of such sections to adapt the housing or cylinder to various penis diameter or girth sizes.

FIG. 30 illustrates how a flange section 15''' can be made as a separate component of cylinder 10 so as to be removable and replaceable with sections 15''' which fit better with different size and girth penises. The section 15''' has a circular flange which can sealingly and frictionally engage with an end of any of the cylinders disclosed herein. The invention also contemplates utilizing a number of such sections 15''' to adapt the cylinder to various penis diameter sizes or girths, such that the system or device can be provided or packaged with different sized flange sections 15'''. This would allow the user to adapt the device or system to his particular needs.

Figure 31:
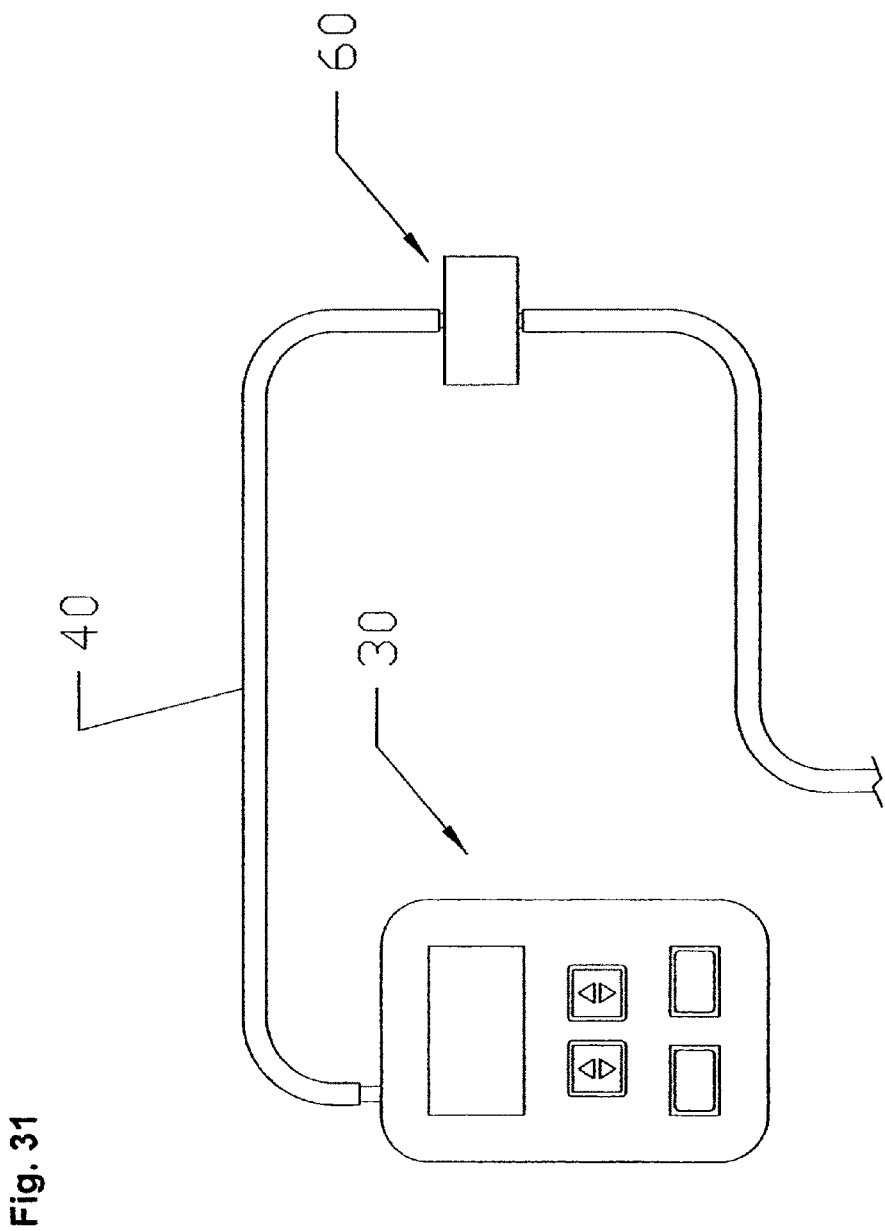
FIG. 31 shows a front view of a controller and/or vacuum supply system connected to a hose and which can be used on any of the herein disclosed embodiments. A valve or filter member ensures that air can be suctioned from the housing or cylinder via the hose but not, e.g., liquids.

FIG. 31 shows a front view of a controller 30 connected to a hose 40 and which can be used on any of the herein disclosed embodiments. A valve or filter 60 has oppositely arranged nipples that connect to serial portions of the hose 40 and is utilized to ensure that air can be suctioned from the cylinder 10 via the hose 40 but not, e.g., liquids. In this way, if the user inadvertently expels urine into the cylinder 10 when the device or system is worn on the user, the valve 60 can prevent such fluids from reaching the controller 30, while allowing air to pass through the valve 60.

Figure 32:
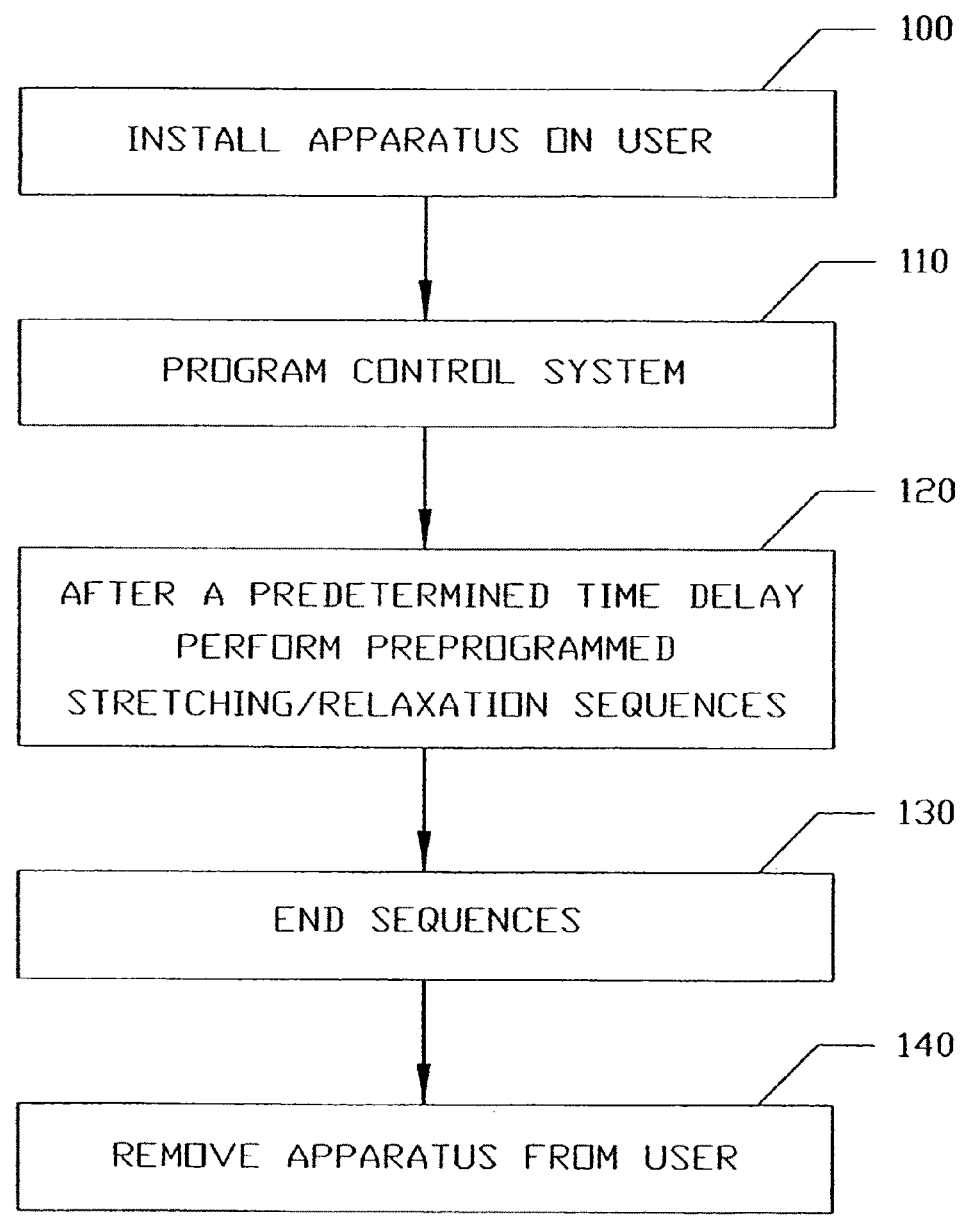
FIG. 32 shows one non-limiting method of practicing the invention using any of the systems and/or devices disclosed herein.

FIG. 32 shows one non-limiting method of practicing the invention using any of the systems and/or devices disclosed herein. By way of example and using the device of FIG. 1, the user first places the garment 20 on his person in step 100. This can be accomplished by the user first installing the cylinder 10 over the penis. Then, the user puts-on the garment 20 while being careful to slide the cylinder 10 through the opening 26. The straps 27 are then connected together in an area of the waist flanks. At this point, the user can connect the nipple 13 to a free end of the hose 40. With the other end of the hose 40 connected to the controller 30, the user can activate the controller 30 to begin operation and ensure that the desired program is set for operation. If not, the user can program the controller 30 in step 110. The user can then lay in bed and fall asleep and eventually reach REM sleep. If the controller 30 is properly programmed, the programmed sequence of causing an erection and then allowing the penis to relax will occur at various times during REM sleep in step 120.

Thus, for example, if the user typically goes to bed at 10:00 PM, reaches REM sleep at or before 11:00 PM, awakes at 7:00 AM, and would normally have three NPT events between 11:00 PM and 7:00 AM, the controller 30 can execute the following exemplary program sequence: Sequence 1—controller 30 causes suction at a first predetermined level, e.g., suction sufficient to cause full erection, for a first predetermined time period, e.g., 30 minutes, and at a first predetermined start time (relative time) measured as two hours from the time that the controller 30 is activated, e.g., 12:00 PM. This will cause the penis to assume a first nighttime erection. The controller 30 then turns off the suction for a predetermined time period, e.g., 60 minutes, and at a predetermined time, e.g., 12:30 PM, thereby allowing the penis to relax. The controller 30 then causes suction again at a second predetermined level, for a second predetermined time period, e.g., 30 minutes, and at a second predetermined start time, e.g., 1:30 AM. This will cause the penis to assume a second nighttime erection. Then, the controller 30 turns off the suction for a predetermined time period, e.g., 60 minutes, and at a predetermined time, e.g., 2:00 AM. The controller 30 then causes suction again at a third predetermined level, for a third predetermined time period, e.g., 30 minutes, and at a third predetermined start time, e.g., 3:00 AM. Then, the controller 30 turns off the suction for the remaining portion of the night thereby ending the sequences as in step 130. Finally, when the user awakes, he can remove the device shown in FIG. 1 in step 140 and store it for reuse the next night. Preferably, the device is utilized to cause between 3 and 5 erection cycles each night and for between about 30 and 60 minutes each.

Figure 33:
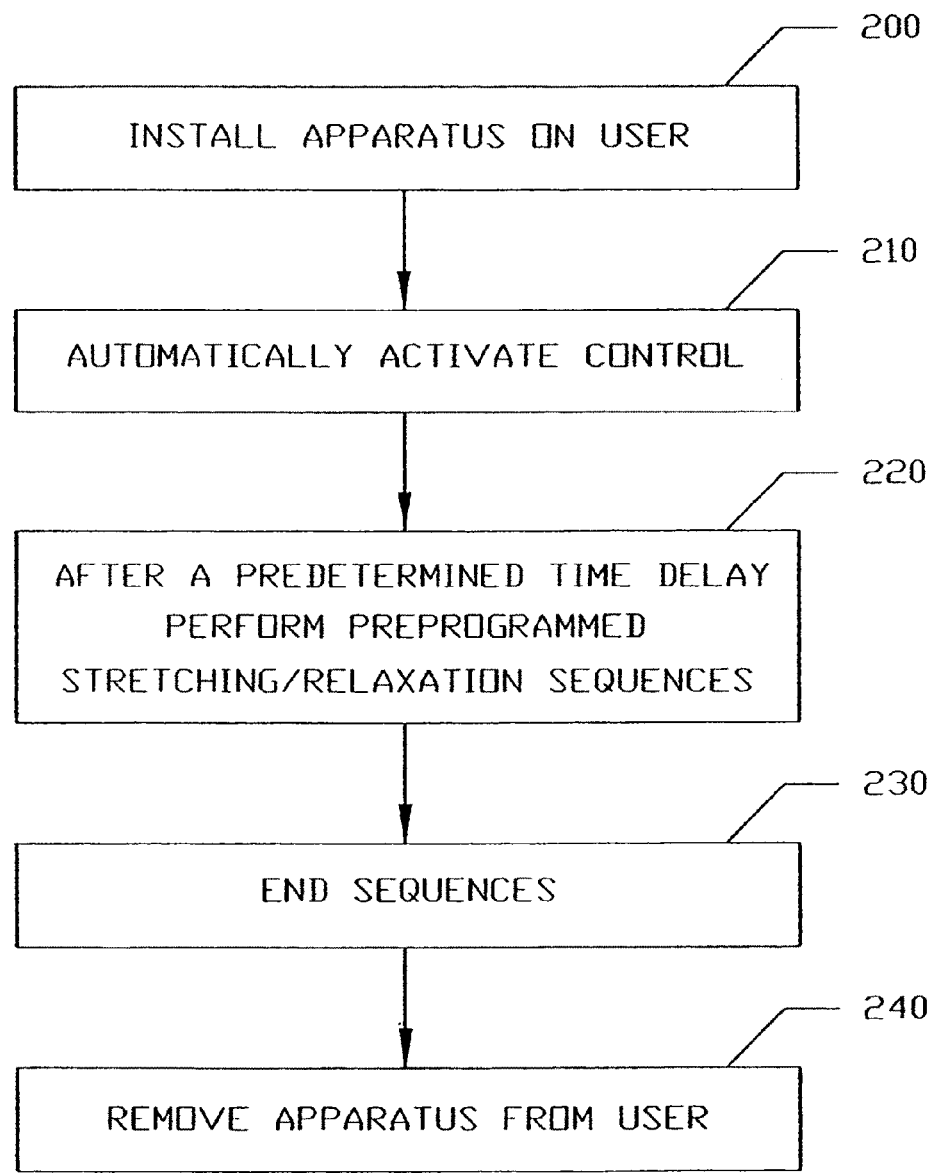
FIG. 33 shows another non-limiting method of practicing the invention using any of the systems and/or devices disclosed herein.

FIG. 33 shows another non-limiting method of practicing the invention using any of the systems and/or devices disclosed herein. By way of example and using the device of FIG. 1, the user first places the garment 20 on his person in step 200. This can be accomplished in the same as step 100. The user can then lay in bed and fall asleep and eventually reach REM sleep. Since the controller 30 is properly programmed to run an automatic sequence which can be programmed by, e.g., date, so that a particular sequence runs on a particular date, the sequence of causing an erection and then allowing the penis to relax will automatically occur at various times during REM sleep in step 220.

Thus, for example, if the user, as in the previous example, typically goes to bed at 10:00 PM, reaches REM sleep at or before 11:00 PM, awakes at 7:00 AM, and would normally have three NPT events between 11:00 PM and 7:00 AM, the controller 30 can execute the following exemplary program sequence: Sequence 1—controller 30 causes suction at a first predetermined level, e.g., suction sufficient to cause full erection, for a first predetermined time period, e.g., 30 minutes, and at a first predetermined start time (relative time) measured as two hours from the time that the controller 30 is activated, e.g., 12:00 PM. This will cause the penis to assume a first nighttime erection. The controller 30 then turns off the suction for a predetermined time period, e.g., 60 minutes, and at a predetermined time, e.g., 12:30 PM, thereby allowing the penis to relax. The controller 30 then causes suction again at a second predetermined level, for a second predetermined time period, e.g., 30 minutes, and at a second predetermined start time, e.g., 1:30 AM. This will cause the penis to assume a second nighttime erection. Then, the controller 30 turns off the suction for a predetermined time period, e.g., 60 minutes, and at a predetermined time, e.g., 2:00 AM. The controller 30 then causes suction again at a third predetermined level, for a third predetermined time period, e.g., 30 minutes, and at a third predetermined start time, e.g., 3:00 AM. Then, the controller 30 turns off the suction for the remaining portion of the night thereby ending the sequences as in step 230. Finally, when the user awakes, he can remove the device shown in FIG. 1 in step 240 and store it for reuse the next night.

Figure 34:
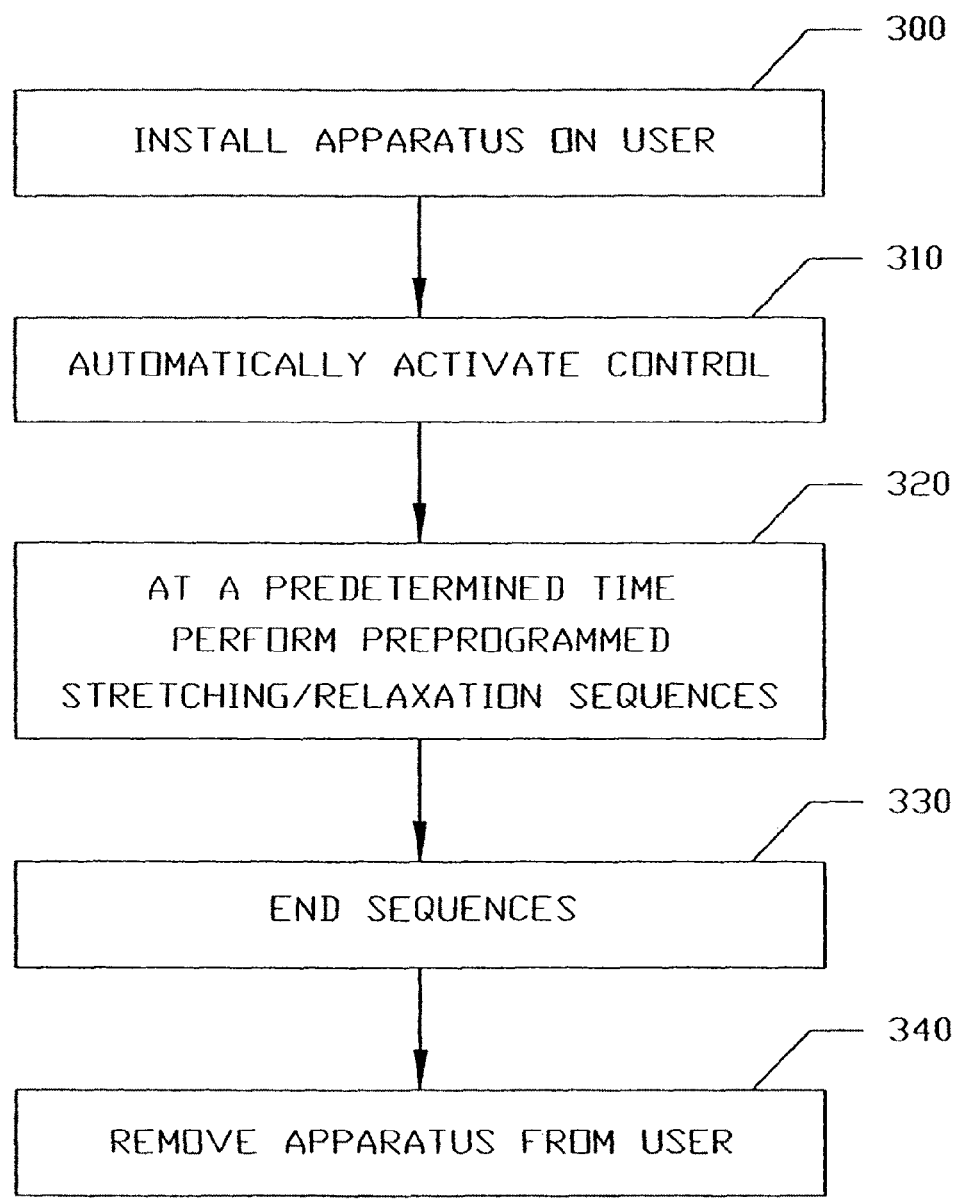
FIG. 34 shows another non-limiting method of practicing the invention using any of the systems and/or devices disclosed herein.

FIG. 34 shows another non-limiting method of practicing the invention using any of the systems and/or devices disclosed herein. By way of example and using the device of FIG. 1, the user first places the garment 20 on his person in step 300. This can be accomplished in the same as steps 100 and 200. The user can then lay in bed and fall asleep and eventually reach REM sleep. Since the controller 30 is properly programmed to run an automatic sequence which can be programmed by, e.g., date, so that a particular sequence runs on a particular date, the sequence of causing an erection and then allowing the penis to relax will automatically occur at various times during REM sleep in step 320.

Thus, for example, if the user, as in the previous example, typically goes to bed at 9:00 PM, reaches REM sleep at or before 11:00 PM, awakes at 7:00 AM, and would normally have three NPT events between 11:00 PM and 7:00 AM, the controller 30 can execute the following exemplary program sequence: Sequence 1—controller 30 causes suction at a first predetermined level, e.g., suction sufficient to cause full erection, for a first predetermined time period, e.g., 30 minutes, and at a first predetermined start time which, in the embodiment of FIG. 34 is the actual time that the controller 30 was programmed to start the first sequence (absolute time—as determined by the internal clock of the controller 30), e.g., 12:00 PM. This will cause the penis to assume a first nighttime erection. The controller 30 then turns off the suction for a predetermined time period, e.g., 60 minutes, and at a predetermined time, e.g., 12:30 PM, thereby allowing the penis to relax. The controller 30 then causes suction again at a second predetermined level, for a second predetermined time period, e.g., 30 minutes, and at a second predetermined start time, e.g., 1:30 AM. This will cause the penis to assume a second nighttime erection. Then, the controller 30 turns off the suction for a predetermined time period, e.g., 60 minutes, and at a predetermined time, e.g., 2:00 AM. The controller 30 then causes suction again at a third predetermined level, for a third predetermined time period, e.g., 30 minutes, and at a third predetermined start time, e.g., 3:00 AM. Then, the controller 30 turns off the suction for the remaining portion of the night thereby ending the sequences as in step 330. Finally, when the user awakes, he can remove the device shown in FIG. 1 in step 340 and store it for reuse the next night.

Figure 35A:
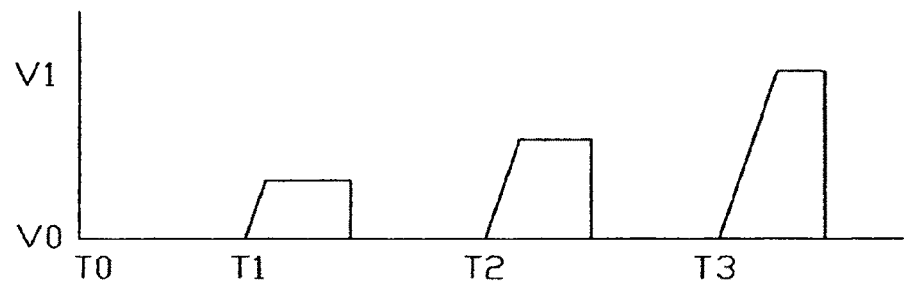
FIGS. 35A-35C show various non-limiting vacuum programs which can be implemented according to the invention and using any of the systems and/or devices disclosed herein. The values T1-T3 are indicative of time start points, e.g., 11:00 PM, 1:00 AM, and 3:00 AM. The values V0 and V1 are indicative, respectively of low or no-vacuum and a maximum vacuum level. Preferably, a minimum vacuum is provided and/or maintained in the housing between erection causing events.
Figure 35B:
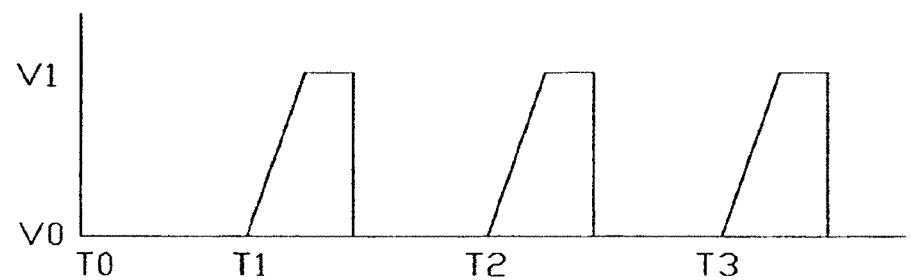
Figure 35C:
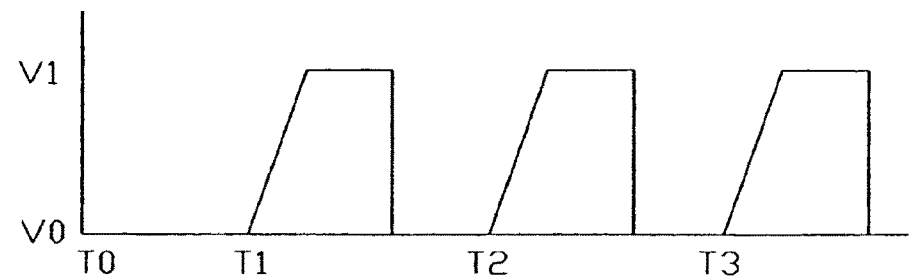

FIGS. 35A-35C show various non-limiting sequence programs for the controller 30 which can be implemented according to the invention and using any of the systems and/or devices disclosed herein. The values T1-T3 are indicative of time start points which can be either relative start times or absolute start times. An example of a relative start time is as follows: with activation at 9:00 PM and a two hour start time delay, the controller 30 will start the first sequence at a T1 of 11:00 PM. An example of an absolute start time is as follows: with activation at 9:00 PM and a programmed first sequence start time of 11:00 PM, the controller 30 will start the first sequence at a T1 of 11:00 PM when its internal clock detects that the time is 11:00 PM. The value V0 indicates a no-vacuum or preferably a minimum vacuum level. The value V1 indicates a maximum vacuum level. Preferably, a minimum vacuum is provided and/or maintained in the cylinder 10 between erection causing events, i.e., during penis relaxation. FIG. 35A shows an increasing amount of vacuum used at three different NPT events or sequences with three different time periods of maximum vacuum throughout night-time. This sequence can be advantageous in the case of a user who requires a transition period before being subjected to full NPT events. FIG. 35B shows a steady and shorter amount, e.g., 20 minutes, of vacuum at three different time periods throughout night-time. FIG. 35C shows a steady and longer amount, e.g., 40 minutes, of vacuum used at three different NPT events throughout night-time. Various combinations of such programs can be tailored to the use based on professional recommendations and can preferably be designated by medical professional such as a doctor under a treatment program, especially in the case of the user being treated to restore and/or maintain penile length when the user has diminished or loss of NPT and/or ED following a surgical procedure such as radical retropubic prostatectomy.

Figure 37:
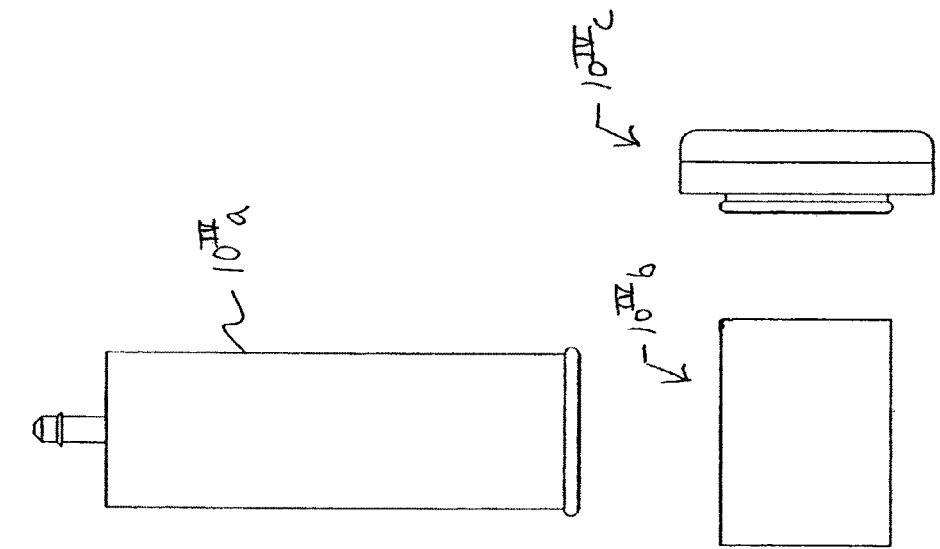
FIG. 37 illustrates the cylinder shown in FIG. 36 in a disassembled state.
Figure 36:
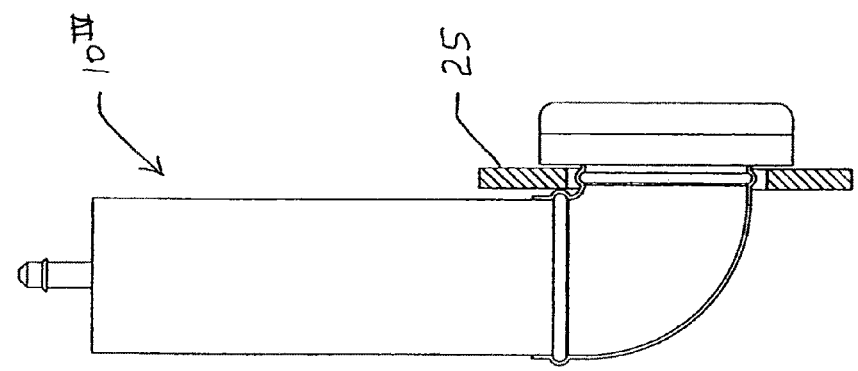
FIG. 36 shows another non-limiting way in which a cylinder can be used with the garment.
Figure 40:
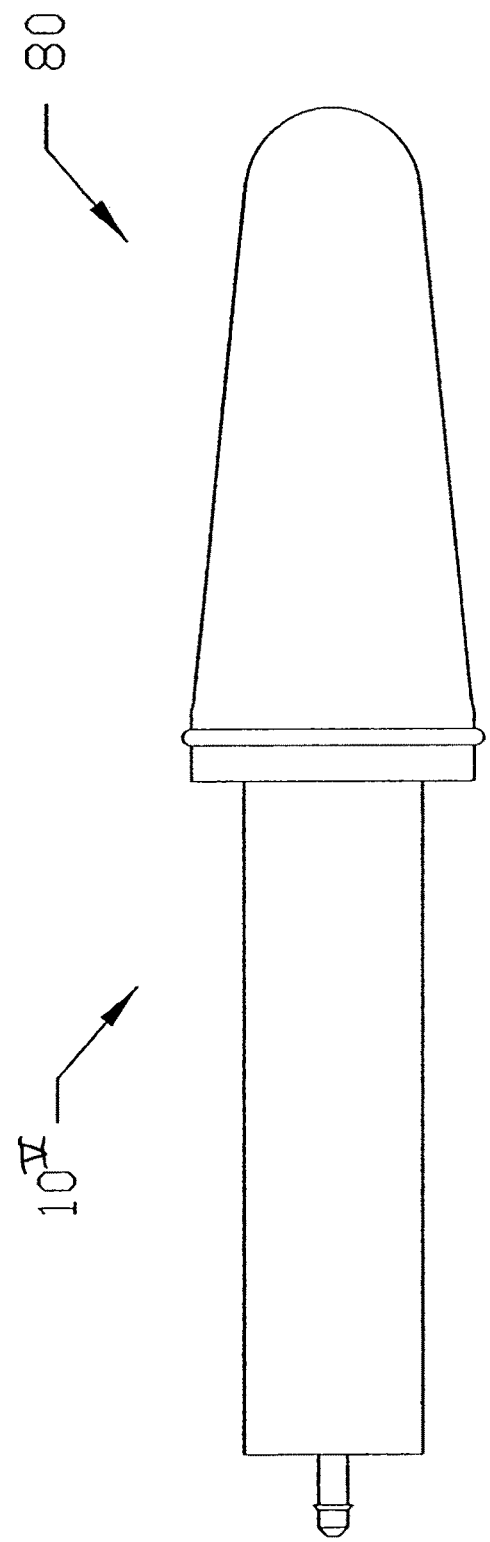
FIG. 40 shows the cylinder and sheath of FIG. 39 in an assembled state and prior to the penis receiving end of the sheath being folded into the distal end of the cylinder.
Figure 43:
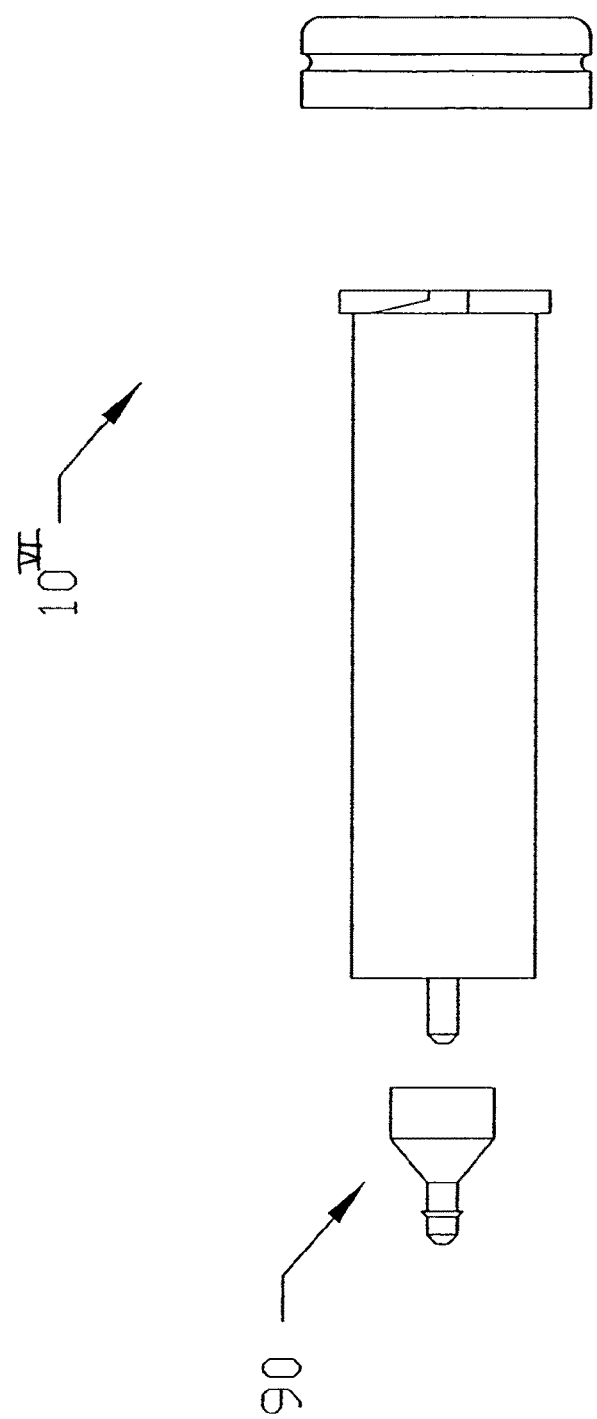
FIG. 43 shows another non-limiting embodiment of a cylinder system that can be used in accordance with the invention. This embodiment is similar to that shown in FIG. 38 except that it utilizes a quick-release tip in addition to the cylinder main body and the disconnectable distal ring.
Figures 44, 45:
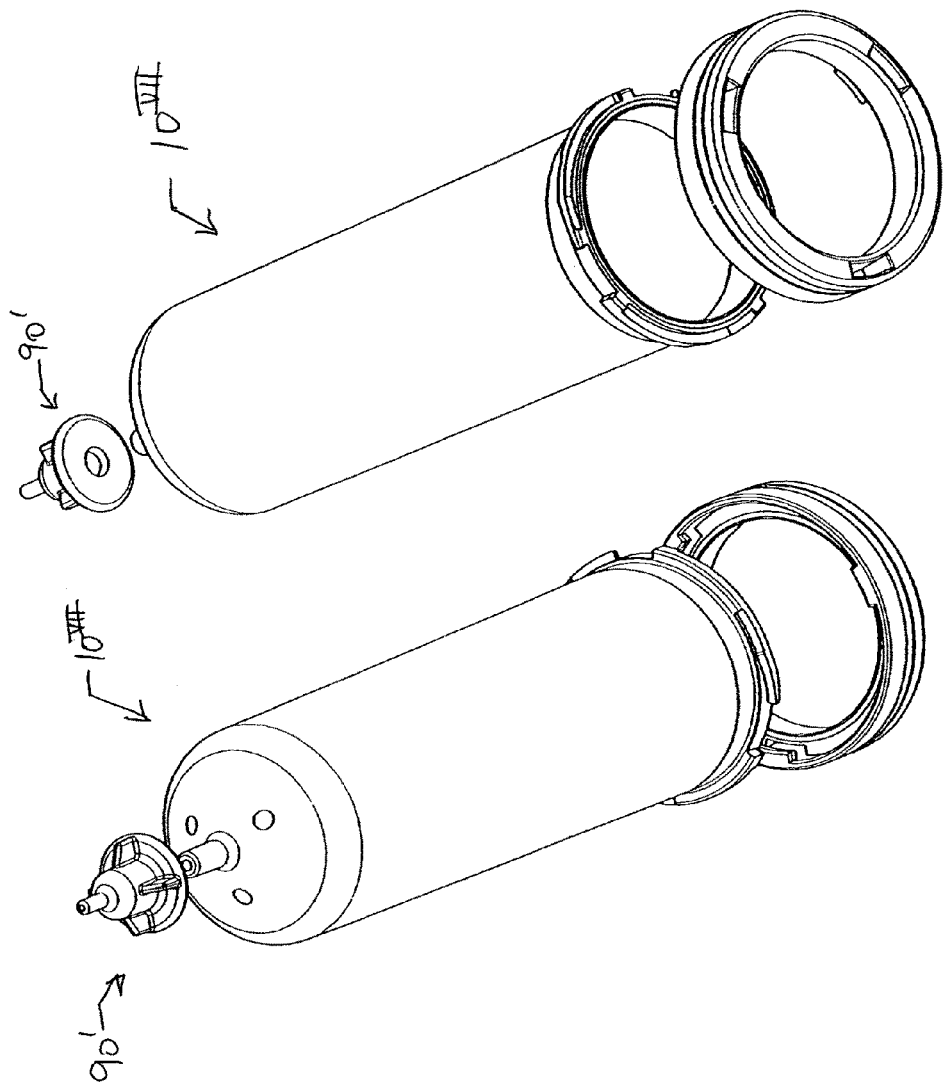
FIGS. 44 and 45 show front-side and rear-side perspective views of another non-limiting embodiment of a cylinder system that can be used in accordance with the invention in an disassembled state.
Figure 46:
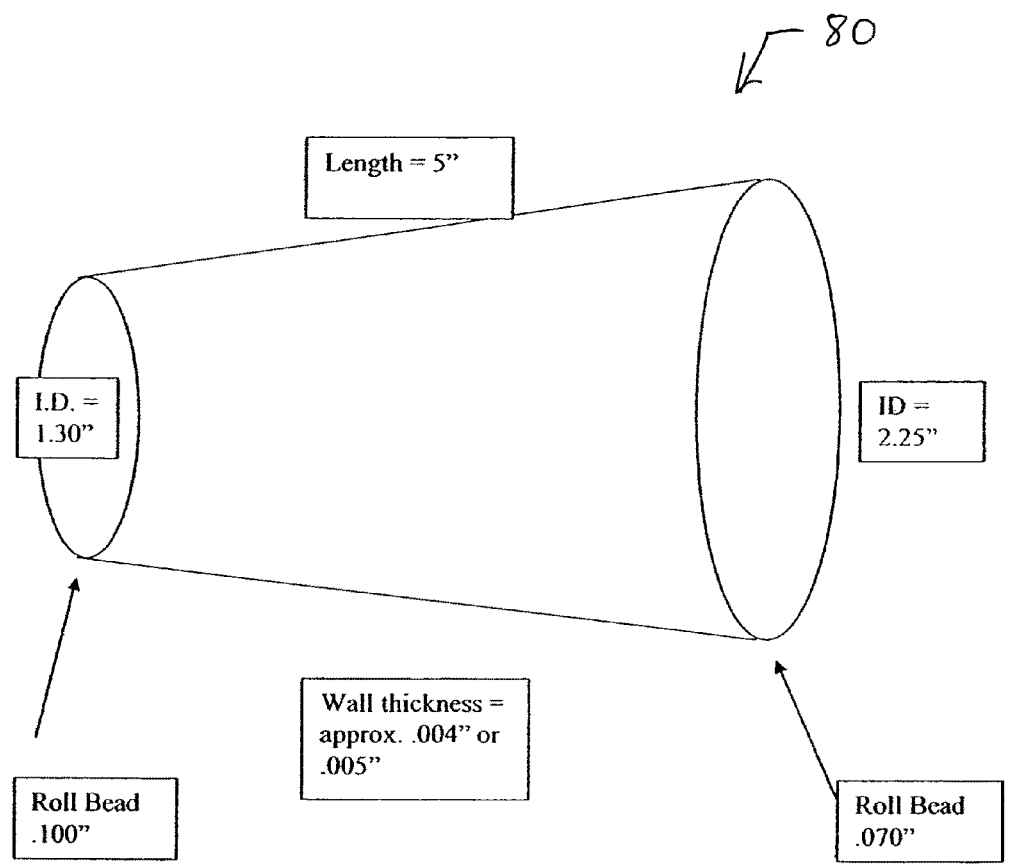
FIG. 46 shows a non-limiting embodiment of a sheath with size dimensions which can be used in any of the cylinder embodiments disclosed herein.

The invention also contemplates utilizing a cylinder having a straight shape, rather than a bent one as in the previous embodiments. The straight cylinder can utilize a conformable base that forms the seal against the skin of the penis. The conformable base can be a latex or polyurethane material, similar to a condom, but open on both ends so that one end can be secured to the cylinder and the other end could be rolled onto the base of the penis or attached to a flange section. In this regard, FIG. 36 shows another non-limiting way in which a cylinder $10^{IV}$ can be used with the garment and FIG. 37 illustrates the cylinder $10^{IV}$ shown in FIG. 36 in a disassembled state. The cylinder $10^{IV}$ utilizes a main body portion $10^{IV}a$ which can have the same configuration as previous embodiments as regards its proximal end. The distal end, however, utilizes one or more circumferential projections in order to allow one end of a flexible sleeve member $10^{IV}b$ to sealingly engage with the distal end of member $10^{IV}a$. The flange section member $10^{IV}c$ can have the same configuration as previous embodiments as regards its flange section. However, member $10^{IV}c$ utilizes one or more circumferential projections in order to allow another end of a flexible sleeve member $10^{IV}b$ to sealingly engage with the member $10^{IV}c$. By way of non-limiting example, the flexible member $10^{IV}b$ can be made of materials similar to those utilized in condoms. Alternatively, the member $10^{IV}c$ can be dispensed with so that the cylinder member $10^{IV}$ utilizes only members $10^{IV}a$ and $10^{IV}b$ with one end of the member $10^{IV}b$ having a circular rim similar to that of a condom so as to provide sealing to a base portion of the penis.

Figure 48:
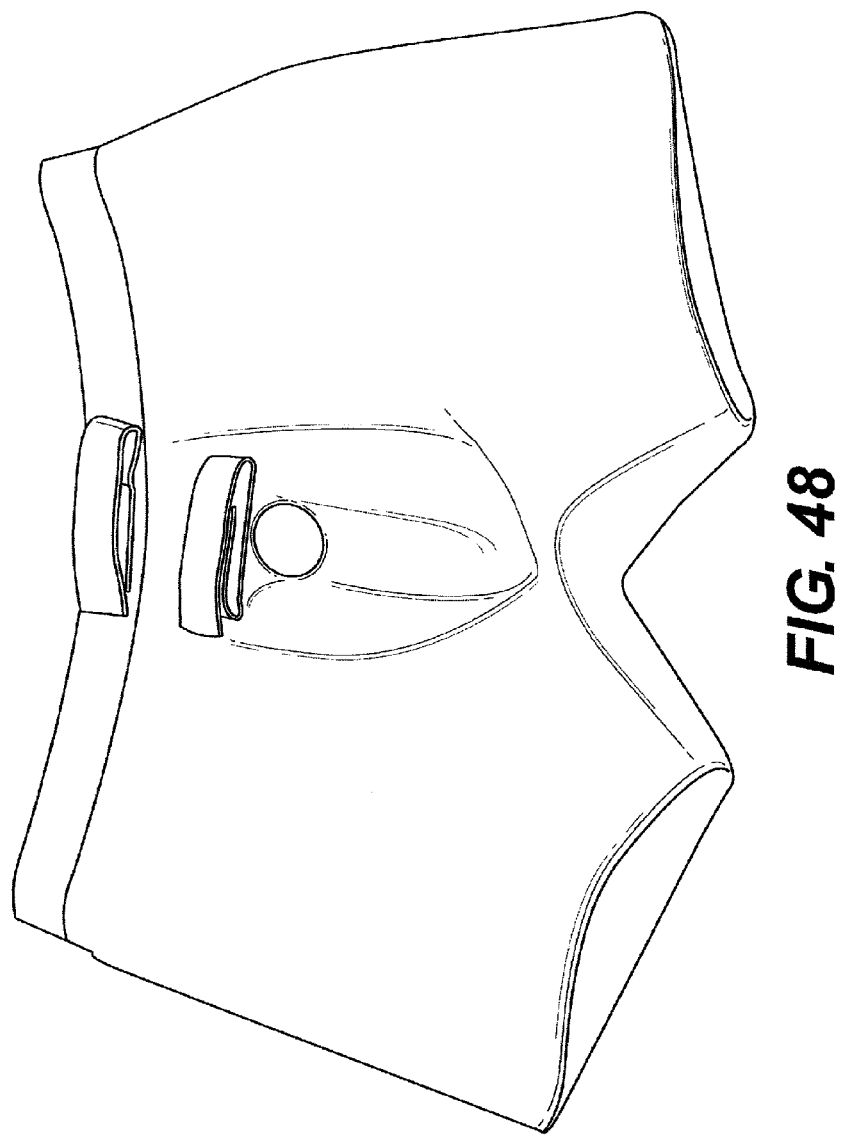
FIG. 48 shows a non-limiting embodiment of an alternative undergarment which can be used with any of the cylinder and controller embodiments disclosed herein.

FIGS. 39-43 show another non-limiting embodiment of a cylinder system which can be used with an undergarment of the type disclosed herein. This embodiment utilizes a main cylinder section $10^{V}$ and a sheath 80 that can have the general configuration of a condom but is preferably tapered so that the open end is generally larger in diameter. The distal ring can be connected and disconnected from the main cylinder body by, e.g., a rotatable locking connection, as shown in the drawings. Other connections may also be utilized. Furthermore, an outer surface of the distal ring can be provided with a friction surface to allow the user to more easily grip the distal ring and rotate it (relative to the cylinder main body) to the lock and unlocked position. The sheath 80 has an enlarged open end whose circular rim is sized and configured to fit over and into a ring-shaped recess formed on an outer surface of the distal ring of the cylinder section $10^{V}$ (see FIG. 40). This embodiment can be used so that the distal ring is arranged inside the garment (see FIG. 8) or preferably outside the garment (see FIG. 42). Furthermore, as with the other embodiments, the instant embodiment can preferably be used with the garment shown in FIG. 48, but is also usable with garments of the type shown in, e.g., FIGS. 1-28.

Figure 47:
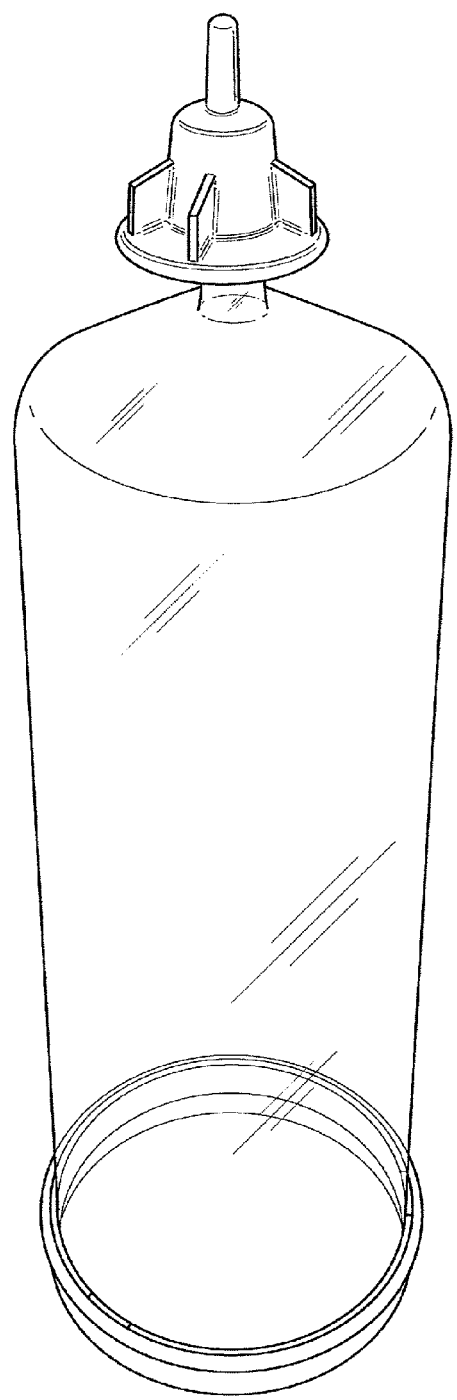
FIG. 47 shows another non-limiting embodiment of a cylinder that can be used in accordance with the invention. This embodiment is similar to that shown in FIGS. 44 and 45 except that it utilizes a transparent cylinder main body and a solid colored quick-release tip and distal ring.

FIGS. 43-47 show other non-limiting embodiments of cylinder systems $10^{VI}$, $10^{VII}$ utilizing a quick release 90, 90' which can be used with any undergarment of the type disclosed herein. These embodiments utilize a main cylinder section $10^{VI}$, $10^{VII}$ having a removable distal ring, a sheath, and a quick-release tip 90, 90'. The quick-release tip 90, 90' has a proximal end which can be connected to the vacuum hose 40 (see e.g., FIG. 1) and a distal end which is removably connected to the nipple of the cylinder 10. This device 90, 90' functions as a safety device and allows the user to quickly and mechanically disconnect the vacuum from the cylinder by gripping the member 90, 90' and twisting it off of the cylinder $10^{VI}$, $10^{VII}$. The embodiment shown in FIG. 47 illustrates the embodiment shown in FIGS. 44 and 45 utilizing a transparent main body. Furthermore, as with the other embodiments, the instant embodiment can preferably be used with the garment of the type shown in FIG. 48.

A particularly preferred non-limiting embodiment of the system of the invention would utilize a control of the type shown in FIGS. 13-15. Preferably, the control is of the type assembled by the company The Dynamic Group of Minnesota which can be manufactured for Assignee Alagin Research LLC. The particularly preferred non-limiting embodiment of the system of the invention would also utilize a cylinder system of the type shown in FIGS. 44, 45 and 47. Preferably, the cylinder system is of the type assembled by the company The Dynamic Group of Minnesota having part numbers DG tool 7067, DG tool 7068, and DG tool 7162, which can be manufactured for Assignee Alagin Research LLC. The particularly preferred non-limiting embodiment of the system of the invention would further utilize a garment of the type shown in FIG. 48. Such garments can be manufactured by companies which typically manufacture such garments and can be made in different sizes to accommodate men of various size ranges. The sheath can preferably have the approximate size dimensions shown in FIG. 46.

The invention also contemplates utilizing at least one emergency vacuum release device or system. By way of non-limiting example, such a device can be incorporated into and/or onto the cylinder (as in the case of device 90, 90') and/or the controller. A redundant safety feature of a vacuum release on both the controller and cylinder would be preferable.

The invention also contemplates utilizing at least one sensor alarm device or system that is activated when, e.g., a) the vacuum pump is non-operational and/or b) the vacuum pump is operational and no vacuum is achieved due to a leak or poor seal.

The invention also provides that the system and method discussed are used and/or meet applicable existing and/or specific FDA restrictions on similar vacuum erection devices. The controller's operation can thus be made consistent with such requirements. For example, the controller can provide between a minimum of 5 minutes of vacuum to a maximum of 30 minutes of vacuum per cycle with at least 60 minutes of intervening time between cycles with no vacuum.

The invention also provides that the system and method discussed and/or shown in the drawings which is utilized to treat or address diminished NPT and/or ED resulting from any pathological process or medical condition. Non-limiting general conditions which can possibly benefit from the invention include cardiovascular disease, peripheral vascular disease (including atherosclerosis and endothelial dysfunction), hormonal imbalance (testosterone deficiency). Non-limiting examples of ways in which the invention can be utilized are discussed hereafter:

Prostatectomy

According to data from the National Cancer Institute, NIDDK, American Cancer Society, and the US Census Bureau, approximately 160,000-190,000 men were newly diagnosed with prostate cancer in 2002, and over 230,000 men were diagnosed in 2004. Whether this increased incidence is due to a rise in the actual number of cases or increased detection in light of more aggressive and/or more sensitive screening remains unknown. As of November 2007, SEER (Surveillance, Epidemiology and End Results) based data indicate that the complete prevalence of prostate cancer (all ages and races) in the United States was approximately 2.1 million men. While the number of men diagnosed with prostate cancer that choose watchful waiting or deferred therapy may be increasing, this cohort is likely to remain small until a broad consensus is reached within the medical community. Thus, it may be assumed that most men diagnosed with prostate cancer will elect radiation or surgical treatments. Preferably, the invention can be used as part of a treatment and/or prevention and/or rehabilitation program on at least some of the members of this group, as discussed above.

Diabetes

In diabetic men, the prevalence of ED has been estimated to be between 35-50%, although in various cross-sectional studies of diabetic men, the prevalence of ED ranges from 20 to 71%. It is likely that the lower ranges represent moderate and/or complete ED, whereas the higher prevalence is reflective of all levels of severity. In 2005, it was estimated that 20.8 million people (7% of the population) had diabetes in the US. Of these, 10.9 million were men (10.5% of all men over the age of 20). Given that 14.6 million of the 20.8 million predicted cases of diabetes were confirmed by clinical diagnosis, 30% of the diabetic population may remain unaware or untreated. Extrapolating these statistics to the population of diabetic men yields 7.6 million men who were diagnosed with diabetes. Incidence data from 2005 suggests that 1.5 million new cases of diabetes are diagnosed in people over the age of 20 each year. Assuming that 52.4% of these are men (direct calculation of prevalence data above), 786,000 adult men will be diagnosed with diabetes each year. Assuming that 30% of diabetic men experience significant ED, it is assumed that a similar proportion of men also have sufficient deficits in peripheral tissue function (vascular/neurogenic dysfunction or fibrosis) and may be at risk for penile length changes. This yields a total population of roughly 3.3 million diabetic men who are at risk and 240,000 diabetic men who become newly at risk annually. Preferably, the invention can be used as part of a treatment and/or prevention and/or rehabilitation program on at least some of the members of this group, as discussed above.

Penile Prosthesis Implants

In 1994, it was estimated that 300,000 men have undergone penile implant surgery since 1973. While there is insufficient data to determine the number of men who currently have penile prostheses, 30-40% of men with ED may be candidates for penile prostheses implantation. Interestingly, recent estimates indicate that 10,000-15,000 patients elect to receive a penile implant each year, suggesting that most men do not choose this option. Anecdotal reports suggest that men with penile prostheses experience either actual or perceived shortening of the penis. Preferably, the invention can be used as part of a treatment and/or prevention and/or rehabilitation program on at least some of the members of this group, as discussed above.

Peyronie's Disease

The prevalence of Peyronie's disease has been estimated to be 1% of the male population or 1.4 million men in the US. The incidence of Peyronie's disease is estimated to be approximately 1-3% in the US, although most experts agree that this figure is likely to be an underestimate. Recent research by Dr. John Mulhall suggests that the incidence is far higher at approximately 8.9%. Assuming a consistent baseline of 1.4 million men that have been diagnosed, and that 5% of these men will utilize the instant invention, approximately 70,000 men may benefit from the invention each year. Using the incidence rate of 1%, there may be an additional 70,000 men who are likely to benefit from the invention annually. Preferably, the invention can be used as part of a treatment and/or prevention and/or rehabilitation program on at least some of the members of this group, as discussed above.

Scleroderma

ED is commonly cited as being one of the first symptoms in men with scleroderma. The overall prevalence of scleroderma has been estimated to be 300,000 in the US. However, this condition is three times more common in women. Thus, an estimated 75,000 men in the US are likely to have scleroderma. Incidence data suggest that 6,000 adults (1500 men) are newly diagnosed each year in the US. Preferably, the invention can be used as part of a treatment and/or prevention and/or rehabilitation program on at least some of the members of this group, as discussed above.

Multiple Sclerosis

ED is also common in neurodegenerative syndromes like multiple sclerosis. In 2004, the Multiple Sclerosis Foundation and the NIH estimated that 250,000 to 500,000 cases of multiple sclerosis were diagnosed in the US. Since multiple sclerosis is twice as likely to be diagnosed in women, the adult male population in the US is estimated to be 83,000-167,000. Preferably, the invention can be used as part of a treatment and/or prevention and/or rehabilitation program on at least some of the members of this group, as discussed above.

It should be noted that the use of the term "erection" herein can, in many cases, be substituted with the term "tumescence" and/or can be substituted with the terms "tumescence/erection" or "tumescence or erection". This is because some users may achieve a full erection, although partial tumescence may be sufficient for the therapeutic effect. Furthermore, non-limiting materials for the cylinder include Bayer Makrolon (polycarbonate formulation), non-limiting materials for the base annulus or distal ring include Basell Purell GB7250 (high density polyethylene formulation), non-limiting materials for the quick-release tip include DuPont Hytrel G3548L (thermoplastic polyester elastomer formulation), and non-limiting materials for the condom member or internal flexible sheath include latex.

The controller(s) can also preferably include a vacuum sensor which can ensure that appropriate levels of vacuum are achieved and maintained without the pump motor being activated at all times. If good sealing is ensured, vacuum can be maintained in the absence of pump activity. Thus, the vacuum pump motor need only operate to maintain set vacuum level(s) for the duration of each cycle, and can be turned off when not needed, thereby decreasing noise and vibration, as well as increasing the comfort level to patients and/or users of the device. The controller(s) is also preferably able to store (in its memory) the total time of vacuum achieved, such that the patient (or user) and the physician can monitor the progression and efficacy of the therapy.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for causing at least one penile erection event, the system comprising:
   a vacuum source and/or supply device;
   a housing configured to at least partially receive therein a penis;
   a housing support system adapted to support the housing on a user in a non-perpendicular orientation relative to a frontal plane of a body of the user and utilizing at least one connector coupled to an outside surface of the housing and being located between opposite ends of the housing, wherein the housing is adapted to be secured about the user in the non-perpendicular orientation utilizing the at least one connector so as to be usable at least during sleep;
   a sheath having one end adapted to be coupled to the housing and comprising at least one of:
   a tapered section;
   a roll bead arranged on a larger diameter end; and
   opposite ends having different inside diameters; and
   a controller which activates a pre-determined sequence of erection cycles or events.

2. The system of claim 1, wherein the housing support is wearable by the user and the system is structured and arranged to be usable during REM sleep.

3. The system of claim 1, wherein the controller is separated from the housing, connected to the housing via a hose, and is programmed to perform the pre-determined sequence of erection cycles or events during sleep.

4. The system of claim 3, wherein the controller executes the pre-determined sequence of erection cycles or events based on a doctor's prescription.

5. The system of claim 3, wherein the controller is at least one of:
   portable;
   securable to a garment; and
   removably arranged on a garment.

6. The system of claim 3, wherein the controller and the vacuum source and/or supply device are arranged on a single device.

7. The system of claim 3, wherein the controller and the vacuum source and/or supply device are arranged on a portable device.

8. The system of claim 3, wherein the controller and the vacuum source and/or supply device are arranged on a device which has a power supply.

9. The system of claim 8, wherein the device having the controller, the vacuum source and/or supply device, and the power supply is connected to the housing via at least one of:
   a conduit;
   a hose; and
   a flexible tube.

10. The system of claim 1, wherein the controller is programmed to cause penile erections in a manner which addresses, treats, or attempts to treat, one or more conditions caused by ageing, disease or medical/surgical interventions.

11. The system of claim 1, wherein the sheath comprises each of:
    the tapered section;
    the roll bead arranged on the larger diameter end; and
    opposite ends having different inside diameters.

12. The system of claim 1, wherein the housing support system comprises at least one strap connector coupled to the housing and at least one strap connectable to the at least one strap connector.

13. The system of claim 1, wherein the housing support system comprises at least one strap wearable by a user during sleep and connectable to at least one strap connector coupled to the housing.

14. The system of claim 1, wherein the housing comprises at least one of:
    a distal flange; and
    a distal flange adapted to connect a distal end of the sheath to the housing.

15. The system of claim 1, wherein the housing support system supporting the housing on a user comprises a surface adapted to contact the user, and wherein the housing is oriented at a non-perpendicular angle in relation to the surface of the support.

16. The system of claim 1, wherein the controller is separated from the housing and is connected thereto via a hose and wherein the housing support system further comprises:
    a base portion structured and arranged to contact a base portion of a user penis; and
    at least one strap connectable about the user and to the at least one connector.

17. A method of treating dysfunction, diminished, or loss of nocturnal penile tumescence (NPT), erectile dysfunction (ED), and/or preventing penile shortening (maintaining penile length) using the system of claim 1, the method comprising:
    mounting the housing about a user's penis; and
    activating the pre-determined sequence of erection cycles or events.

18. The method of claim 17, comprising:
    positioning the housing support system on a user, whereby the housing support system is configured to retain the housing on the user during sleep while the housing at least partially receives therein the user's penis.

19. A method of causing penile erection, the method comprising:
    placing a housing at least partially over or covering a user's penis;
    prior to the placing, connecting one end of a sheath to the housing, wherein the sheath comprises at least one of:
    a tapered section;
    a roll bead arranged on a larger diameter end; and
    opposite ends having different inside diameters;
    supporting the housing on the user in a hands-free manner;
    connecting a control device to the housing, said control device comprising at least one pre-programmed sleep operation sequence structured and arranged to cause erections at a predetermined point in time; and
    causing a vacuum in the housing for at least one predetermined time period while the user is at least one of:
    sleeping;
    positioned in a generally horizontal position;
    being treated for a condition which results in the user having lost, at least partially, the ability to achieve an erection at least during sleep;
    wearing a garment adapted for use with the housing; and
    in REM sleep.

20. The method of claim 19, wherein the medical condition is a condition which results in a user having lost, at least partially, the ability to achieve an erection at least during sleep.

21. The method of claim 19, wherein the medical condition results from radical retropubic prostatectomy.

22. A system for treating at least one symptom of at least one medical condition affecting the penis, the system comprising:
- a vacuum source and/or supply;
- a housing configured to at least partially receive therein a penis;
- said housing being separated from the vacuum source and/or supply and being connected thereto via a hose or conduit;
- at least one connector arranged on an outside surface of the housing in an area located between opposite ends of the housing and being structured and arranged to allow a user to secure and orient the housing for use at least during sleep;
- a sheath having one end adapted to be removably coupled to an end of the housing and comprising at least one of:
  - a tapered section;
  - roll beads arranged on opposite ends;
  - a roll bead arranged on a larger diameter end; and
  - opposite ends having different inside diameters; and
- a controller which activates a pre-determined sequence of erection cycles or events during sleep.

23. The system of claim 22, wherein the pre-determined sequence of erection cycles or events occurs during at least one of:
- night-time sleep; and
- rapid eye movement (REM) sleep.

24. A method of treating a loss of or diminishment of NPT events resulting from erectile dysfunction (ED) using the system of claim 23, the method comprising:
- mounting the housing about a user's penis; and
- activating the pre-determined sequence of erection cycles or events during sleep.

25. A method of restoring and/or providing normal and healthy blood flow (and/or oxygenation) to the penis and/or which can restore or maintain penile length using the system of claim 24, the method comprising:
- following a surgical procedure, using the system on the penis of a user by:
  - mounting the housing about a user's penis; and
  - activating the pre-determined sequence of erection cycles or events during sleep.

26. The method of claim 25, wherein the surgical procedure comprises radical retropubic prostatectomy.

* * * * *